United States Patent
Spedden et al.

(10) Patent No.: US 8,518,431 B2
(45) Date of Patent: Aug. 27, 2013

(54) STEM CELL CAPTURE AND IMMOBILIZATION COATINGS FOR MEDICAL DEVICES AND IMPLANTS

(75) Inventors: Richard H. Spedden, Clarksville, MD (US); Judy Qiu, Baltimore, MD (US); William Borch, Gambrills, MD (US)

(73) Assignee: Bioactive Surgical, Inc., Clarksville, MD (US)

( * ) Notice: Subject to any disclaimer, the term of this patent is extended or adjusted under 35 U.S.C. 154(b) by 0 days.

(21) Appl. No.: 13/543,059

(22) Filed: Jul. 6, 2012

(65) Prior Publication Data

US 2012/0270294 A1   Oct. 25, 2012

Related U.S. Application Data

(62) Division of application No. 12/537,409, filed on Aug. 7, 2009.

(60) Provisional application No. 61/086,912, filed on Aug. 7, 2008, provisional application No. 61/153,076, filed on Feb. 17, 2009.

(51) Int. Cl.
*A61F 2/02* (2006.01)
*A01N 63/00* (2006.01)
*A61F 2/82* (2006.01)
*A01N 63/02* (2006.01)

(52) U.S. Cl.
USPC .................. 424/423; 424/93.1; 424/93.7

(58) Field of Classification Search
USPC ........................ 424/93.1, 93.7, 423
See application file for complete search history.

(56) References Cited

U.S. PATENT DOCUMENTS

| | | | |
|---|---|---|---|
| 2,197,717 A | 4/1940 | Bradshaw | |
| 2,643,765 A | 6/1953 | Bradshaw | |
| 3,338,401 A | 8/1967 | Regan, Jr. | |
| 4,027,676 A | 6/1977 | Mattei | |
| 4,128,173 A | 12/1978 | Lazarus | |
| 4,366,901 A | 1/1983 | Short | |
| 4,886,604 A | 12/1989 | Sleytr et al. | |
| 5,032,638 A | 7/1991 | Wang et al. | |
| 5,173,365 A | 12/1992 | Singh et al. | |
| 5,188,837 A | 2/1993 | Domb et al. | |
| 5,217,492 A | 6/1993 | Guire et al. | |
| 5,221,535 A | 6/1993 | Domb | |
| 5,227,165 A | 7/1993 | Domb et al. | |
| 5,340,588 A | 8/1994 | Domb | |
| 5,438,041 A | 8/1995 | Zheng et al. | |
| 5,780,062 A | 7/1998 | Frank et al. | |
| 5,824,337 A | 10/1998 | Mullen | |
| 5,840,083 A | 11/1998 | Braach-Maksvytis | |
| 6,051,698 A | 4/2000 | Janjic et al. | |
| 6,174,333 B1 | 1/2001 | Kadiyala et al. | |
| 6,264,675 B1 | 7/2001 | Brotz | |
| 6,284,267 B1 | 9/2001 | Aneja | |
| 6,284,375 B1 | 9/2001 | Jin et al. | |
| 6,291,528 B1 | 9/2001 | Scott | |
| 6,291,811 B1 | 9/2001 | Ogawa | |
| 6,322,810 B1 | 11/2001 | Alkan-Onyuksel et al. | |
| 6,333,029 B1 | 12/2001 | Vyakarnam et al. | |
| 6,395,302 B1 | 5/2002 | Hennink et al. | |
| 6,528,092 B2 | 3/2003 | Mullen | |
| 6,596,699 B2* | 7/2003 | Zamora et al. | 514/44 R |
| 6,835,394 B1 | 12/2004 | Discher et al. | |
| 6,838,493 B2 | 1/2005 | Williams et al. | |
| 6,884,842 B2 | 4/2005 | Sloane et al. | |
| 7,030,127 B2 | 4/2006 | Nathan et al. | |
| 7,052,719 B2 | 5/2006 | Bernstein et al. | |
| 7,097,662 B2 | 8/2006 | Evans, III et al. | |
| 7,148,031 B2 | 12/2006 | Mullen | |
| 7,163,712 B2 | 1/2007 | Chilkoti et al. | |
| 7,211,108 B2 | 5/2007 | Furst et al. | |
| 7,217,427 B2 | 5/2007 | Discher et al. | |
| 7,758,635 B2* | 7/2010 | Parsonage | 623/1.41 |
| 2001/0000470 A1 | 4/2001 | Bernstein et al. | |
| 2002/0048604 A1 | 4/2002 | Mullen | |
| 2002/0197178 A1 | 12/2002 | Yan | |
| 2003/0083740 A1 | 5/2003 | Pathak | |
| 2003/0171558 A1 | 9/2003 | Kadiyala et al. | |
| 2003/0198798 A1 | 10/2003 | Hehrlein et al. | |
| 2003/0216534 A1 | 11/2003 | Chaikof et al. | |
| 2003/0235619 A1 | 12/2003 | Allen et al. | |

(Continued)

FOREIGN PATENT DOCUMENTS

EP   1 920 788 A1   5/2008
WO   WO 91/07171   5/1991

(Continued)

OTHER PUBLICATIONS

Zilberman et al, Journal of Cont. Release 130:202-215, 2008.*
Christopherson, G. et al. "The Influence of Fiber Diameter of Electrospun Substrates on Neural Stem Cell Differentiation and Proliferation", Biomaterials, vol. 30, pp. 556-564, (2009).
Corral, C. et al. "Vascular Endothelial Growth Factor is More Important Than Basic Fibroblastic Growth Factor During Ischemic Wound Healing", Basic Science for Surgeons, vol. 134, pp. 200-205.
Dines, J. et al., "Biologics in Shoulder Surgery: Suture Augmentation and Coating to Enhance Tendon Repair", Techniques in Orthopaedics, vol. 22, pp. 20-25, 2007. (Abstract Only).
Dougherty, Elizabeth, MIT works toward novel therapeutic device, Tech Talk, Harvard-MIT Division of Health Sciences vol. 52, No. 6, Oct. 24, 2007.

(Continued)

*Primary Examiner* — Kevin Hill
(74) *Attorney, Agent, or Firm* — Chalin A. Smith; Smith Patent Consulting

(57) ABSTRACT

Constructs and methods for immobilizing stem and other precursor cells, as well as other bioactive materials of therapeutic value on the surfaces of medical devices, such as bone, cartilage, spinal and tooth implants, are described herein. The present invention has broad application in the incorporation of bioactive and therapeutic materials in or on a medical implant or other interventional device, having particular value in enabling the real-time, utilization by medical personnel of bioactive materials extracted from the patient and subsequently reintroduced and immobilized in an implant device.

10 Claims, 6 Drawing Sheets

(56) References Cited

U.S. PATENT DOCUMENTS

| | | |
|---|---|---|
| 2004/0052836 A1 | 3/2004 | Li et al. |
| 2004/0234576 A1 | 11/2004 | Martin et al. |
| 2005/0002981 A1 | 1/2005 | Lahtinen et al. |
| 2005/0048110 A1 | 3/2005 | Discher et al. |
| 2005/0070959 A1 | 3/2005 | Cichocki, Jr. |
| 2005/0125035 A1 | 6/2005 | Cichocki, Jr. |
| 2005/0158389 A1 | 7/2005 | Domb |
| 2005/0180922 A1 | 8/2005 | Discher et al. |
| 2005/0209145 A1 | 9/2005 | Stupp et al. |
| 2005/0244425 A1 | 11/2005 | McKee et al. |
| 2005/0275123 A1 | 12/2005 | Chopra et al. |
| 2006/0003387 A1 | 1/2006 | Peelle et al. |
| 2006/0047312 A1 | 3/2006 | Olmo |
| 2006/0051395 A1 | 3/2006 | Beyer et al. |
| 2006/0057192 A1 | 3/2006 | Kane |
| 2006/0068416 A1 | 3/2006 | Schluesener et al. |
| 2006/0127950 A1 | 6/2006 | Bosques et al. |
| 2006/0165810 A1 | 7/2006 | Discher et al. |
| 2006/0171986 A1 | 8/2006 | Kuhn et al. |
| 2006/0177495 A1 | 8/2006 | Allen et al. |
| 2006/0205639 A1 | 9/2006 | Domb et al. |
| 2007/0037933 A1 | 2/2007 | Kurth et al. |
| 2007/0141134 A1 | 6/2007 | Kosak |
| 2007/0218123 A1 | 9/2007 | Discher et al. |
| 2008/0058246 A1 | 3/2008 | Bhaskaran et al. |
| 2008/0128296 A1 | 6/2008 | Stopek et al. |
| 2008/0171972 A1 | 7/2008 | Stopek |
| 2008/0188933 A1 | 8/2008 | Koob et al. |
| 2008/0305348 A1 | 12/2008 | Spedden |
| 2009/0099651 A1* | 4/2009 | Hakimi-Mehr et al. ..... 623/1.42 |
| 2009/0148493 A1 | 6/2009 | Ballerstadt et al. |

FOREIGN PATENT DOCUMENTS

| | | |
|---|---|---|
| WO | WO 2005/005767 | 6/2005 |
| WO | WO 2005/086639 * | 9/2005 |
| WO | WO 2007/137117 | 11/2007 |
| WO | WO 2008/007082 | 1/2008 |
| WO | WO 2008/154603 | 12/2008 |

OTHER PUBLICATIONS

Kotwal, VB et al. "Biodegradable Polymers: Which, When and Why?", Indian Journal of Pharmaceutical Sciences, vol. 69, pp. 616-625, 2007.

Mygind, T. "Mesenchymal Stem Cell Ingrowth and Differentiation on Coralline Hydroxyapatite Scaffolds", Biomaterials, vol. 28, pp. 1036-1047, 2007.

Pratten, J. et al. "In Vitro Attachment of *Stapphylococcus epidermidis* to Surgical Sutures With and Without Ag-Containing Bioactive Glass Coating", Journal of Biomaterials Applications, vol. 19, pp. 47-57, 2004.

Rider, C. "Heparin/Heparan Sulphate Binding in the TGF-β Cytokine Superfamily", Biochemical Society Transactions, vol. 34, pp. 458-460, 2006.

Rios, C. "Biologics in Shoulder Surgery: The Role of Adult Mesenchymal Stem Cells in Tendon Repair", Techniques in Orthopaedics, vol. 22, pp. 2-9, 2007.

Schugart, Richard C., et al., "Wound angiogenesis as a function of tissue oxygen tension: A mathematical model", PNAS, Feb. 19, 2008, vol. 105, No. 7, 2628-2633.

Boccaccini, A. R. et al. "Bioactive Composite Materials for Tissue Engineering Scaffolds", Expert Rev Med Devices, vol. 2 (3), pp. 303-317, May 2005. (Abstract Only).

Christopherson, G. et al. "The Influence of Fiber Diameter of Electrospun Substrates on Neural Stem Cell Differentiation and Proliferation", Biomaterials, vol. 30, pp. 556-564, Feb. 2009.

Corral, C. et al. "Vascular Endothelial Growth Factor is More Important Than Basic Fibroblastic Growth Factor During Ischemic Wound Healing", Arch Surg, vol. 134, pp. 200-205, Feb. 1999.

Tuerk, C. et al., "Systematic evolution of ligands by exponential enrichment: RNA ligands to bacteriophage T4 DNA polymerase", Science, vol. 249 (4968):505-510, Aug. 1990.

Deshimaru, R. et al., "Analysis of Fatty Acid Composition in Human Bone Marrow Aspirates", Keio Journal of Medicine, vol. 54 (3), pp. 150-155, Jun. 2005.

Dines, J. et al., "Biologics in Shoulder Surgery: Suture Augmentation and Coating to Enhance Tendon Repair", Techniques in Orthopaedics, vol. 22 (1), pp. 20-25, Mar. 2007. (Abstract Only).

Dougherty, E. et al., "MIT Works Toward Novel Therapeutic Device", Tech Talk, vol. 52 (6), pp. 5, Oct. 2007.

Guo, K.T. et al., "The effect of electrochemical functionalization of Ti-alloy surfaces by aptamer-based capture molecules on cell adhesion", Biomaterials, vol. 28 (3):468-474, Jan. 2007.

King, M. et al., "Using Protein-Functionalized Microchannels for Stem Cell Separation," Proceedings of ICNMM2006, Fourth International Conference on Nanochannels, Microchannels, and Minichannels, Limerick, Ireland, pp. 1-6, Jun. 2006.

Kotwal, V.B. et al. "Biodegradable Polymers: Which, When and Why?", Indian Journal of Pharmaceutical Sciences, vol. 69 (5), pp. 616-625, Sep. 2007.

Middleton, J. et al. "Synthetic Biodegradable Polymers as Medical Devices", Medical Plastics and Biomaterials Archive, vol. 30, Mar. 1998.

Mygind, T. et al., "Mesenchymal Stem Cell Ingrowth and Differentiation on Coralline Hydroxyapatite Scaffolds", Biomaterials, vol. 28, pp. 1036-1047, Feb. 2007.

Pratten, J. et al. "In Vitro Attachment of *Stapphylococcus epidermidis* to Surgical Sutures With and Without Ag-Containing Bioactive Glass Coating", Journal of Biomaterials Applications, vol. 19, pp. 47-57, Jul. 2004.

Qi, L.et al., "Emerging Application of Quantum Dots for Drug Delivery and Therapy", Expert Opinion Drug Delivery, vol. 5(3): 263-267, Mar. 2008.

Rider, C. et al., "Heparin/Heparan Sulphate Binding in the TGF-β Cytokine Superfamily", Biochemical Society Transactions, vol. 34, pp. 458-460, Jun. 2006.

Rios, C. et al., "Biologics in Shoulder Surgery: The Role of Adult Mesenchymal Stem Cells in Tendon Repair", Techniques in Orthopaedics, vol. 22 (1), pp. 2-9, Mar. 2007.

Schugart, R. C., et al., "Wound angiogenesis as a function of tissue oxygen tension: A mathematical model", PNAS, vol. 105 (7), pp. 2628-2633, Feb. 2008.

* cited by examiner

STEM CELL CAPTURE AND IMMOBILIZATION COATINGS FOR MEDICAL DEVICES AND IMPLANTS

PRIORITY

The instant application is a divisional of U.S. patent application Ser. No. 12/537,409 filed Aug. 7, 2009, which, in turn, claims the benefit of U.S. Provisional Application Ser. Nos. 61/086,912 filed Aug. 7, 2008, and 61/1,153,076 filed Feb. 27, 2009, the entire contents of which are incorporated by reference herein.

FIELD OF THE INVENTION

The present invention relates to the immobilization of bioactive materials, such as stem cells, other biological cells, bioactive molecules, particularly growth factors, and other materials of therapeutic value, on internal and/or external surfaces of medical devices, particularly porous implants where bone or tissue ingrowth is desired. In one particular embodiment, the present invention utilizes a high-density nanofilm of amphiphilic molecules to selectively capture, concentrate and immobilize the bioactive material, particularly cellular material, of interest. Such high-density nanofilms, embedded with selective recognition molecules or targeting moieties, may be formed on the surface of a medical device.

The novel constructs and methods of the present invention find particular utility in an operating room environment, enabling medical personnel to coat a prefabricated medical device, such as a bone implant, just prior to use and particularly to utilize bioactive materials extracted from the patient (e.g., autologous and/or endogenous transplant materials), thereby reducing concerns about shipment and storage of bioactive materials as well as adverse immunological reactions caused by genetic incompatibilities or transmission of infective agents.

BACKGROUND OF THE INVENTION

Porous medical implant devices, particularly of metallic, ceramic or polymeric construction, but also those of biological origin, have proven of great value as scaffolds for tissue growth in medical applications. Such constructs find particular utility as scaffolds for bone growth, where the porous structure allows the prosthetic device to bind with adjacent bone as cartilage and bone grow into the pores of the device.

Many techniques have been proposed to promote the desired tissue ingrowth, including the incorporation of molecules that stimulate tissue growth, such as growth factor proteins, into the pores of the prosthetic device prior to implantation of the device in the patient. These techniques typically involve surface coating, adsorption onto a metallic surface, conjugation to a polymer surface or void-filling with biodegradable materials. Plastics such as PLA and PEG find particular use in these void-filling applications, although the degradation products of these materials in any significant quantity can impair biological function. Fibrin, collagen and bone-based cements have also been used in these void-filling applications. Other techniques for immobilizing bioactive materials in the porous structure utilizing various types of coatings have also been proposed.

The many examples in the art where therapeutic and/or bioactive materials are incorporated into medical devices are often focused on the use of a limited number of predetermined types of bioactive molecules, such as specific growth factors, which have been produced in a sterile production environment, often by recombinant techniques. Such coating systems are often better suited to a manufacturing environment than a surgical operating room. Additionally, growth factors and other therapeutic materials are found to have complex interactions with each other, all of which are not clearly understood even by those skilled in the art. While selected growth factors introduced from synthetic production have proven to have benefit, they are costly to produce and can provide adverse reactions in the patient. In addition, the selected mix of components may not have the range of therapeutic activities that may be present in endogenous tissues and fluids, such as bone marrow and adipose tissue. Because of this, in certain procedures, surgeons will often extract tissues or fluids from a patient, put it through a separation process, such as centrifugation, select a fraction which is known to be rich in desired materials, such as growth factors, stem cells or progenitor cells, and then re-inject that material into the patient at a point of injury or surgical intervention to promote healing. The present invention is directed towards the capture and utilization of bioactive molecules and biological cells as might be present in a patient's own tissues and fluids, though the novel constructs of the present invention are also compatible with the use of synthetically produced bioactive molecules and biological cells harvested from cell cultures.

Bone marrow for clinical use is typically obtained as an aspirate extracted from a target patient's bone using a syringe-type device. Often the iliac crest, pelvis or pelvic bone is used as a source due to its large size and proximity to the surface of the body. In some applications, the bone marrow is used without modification, but in many cases some form of separation technology, such as centrifugation, is used to concentrate the desired fraction of the bone marrow. Stem cells and bioactive molecules, including cytokines such as growth factors, are often the target of this separation process, though separation through centrifugation tends to select a fraction that also contains a high level of white blood cells and a broad spectrum of molecular components. Cells and molecules of interest can also typically be obtained from adipose, also fat, tissue. Any tissue of the body has potential, muscle and nerve tissue and tissues associated with the reproductive process are also of particular interest. Material extracted from the patient or intended recipient (i.e., autologous transplant material) has several advantages over other sources, including inherent biocompatibility, potential for lower cost, providing a broader spectrum of useful compounds that might have synergistic effects and potentially reduced regulatory issues or faster regulatory approval. When bone marrow derivatives are used in surgery, they are typically reintroduced into the body by injection by syringe into an area of desired activity or into an implant device or scaffold material which is then implanted in the body.

Many of the current techniques of immobilizing bioactive materials on medical devices, such as prosthetic bone implants, are not well-suited to allowing surgical teams to exercise an option to use endogenous bioactive materials. A construct which allows the surgical team to remove bone marrow from the patient and concentrate and immobilize selected bioactive components of such in the device provides advantages in genetic compatibility of the material as well as potentially reduced cost. The key challenges in such a system are the incorporation of a mostly liquid material into a highly porous material and the retention there while the device is being handled and implanted in the patient.

Thus, the present invention addresses a need in the art, providing for the capture and delivery of bioactive molecules and particularly the real-time utilization of extracted tissues and fluid, whether from the intended recipient (i.e., autologous transplant materials) or a selected donor organism (i.e., allogenic, homologous or heterologous transplant materials), as well as materials that are synthetically produced or produced from cell cultures (recombinant transplant materials). In particular, embodiments of the medical device constructs, kits and packaging systems of the present invention have unique and valuable advantages over current art and enable new medical techniques, with particular importance in surgical procedures.

SUMMARY OF THE INVENTION

As noted above, there are no readily available systems in the art for on site treatment of medical devices, such as prosthetic implants, to allow bioactive materials such as stem cells to be immobilized and concentrated on their surfaces, despite the acknowledged benefits thereof. Herein, it was discovered that disposing an amphiphilic film on the surface of a medical device, with a non-polar liquid/film acting as a "binder" therebetween, facilitates the capture, concentration and immobilization a targeted therapeutic cell or molecule in an efficient, expeditious and economical manner. In the context of the present invention, a plurality of amphiphilic molecules spontaneously align at the interface of a relatively non-polar surface or substrate and a relatively polar surrounding environment and assemble into a molecularly thin, extremely dense, and well-oriented film coating. By affording the hydrophilic head of at least some of the amphiphilic molecules with a targeting moiety having a binding affinity for one or more target bioactive material of interest, the present invention enables the rapid extraction and immobilization of such bioactive material upon exposure thereto.

Accordingly it is an object of the present invention to provide a biocompatible device comprising a solid surface having a film of non-polar liquid disposed thereon, the non-polar liquid film having a plurality of amphiphilic molecules disposed as a monolayer thereon, wherein at least one of the amphiphilic molecules includes or incorporates at least one targeting moiety having binding affinity for bioactive material of interest, for example a target molecule or a surface moiety of a target cell.

The present invention contemplates the use of different amphiphilic molecules and/or targeting moieties, having divergent binding affinities, in a single device, so as to enable the capture of a plurality of different bioactive materials, particularly materials having synergistic functionality (e.g., stem cells and growth factors). By the same token, the present invention also contemplates the inclusion of different targeting moieties that target different structures of the same bioactive material (e.g., different epitopes, surface peptides, adhesion molecules, etc.).

In a preferred embodiment, the targeting moiety is a nucleic acid aptamer, antibody, or a product of a phage-display technique. In a particularly preferred embodiment, the amphiphilic molecule is an aptamer conjugated to a hydrocarbon chain of the form $(CH_2)_n$ where n is greater than eight. Alternatively, the amphiphilic molecule is a conjugation of biotin, avidin and either an aptamer or antibody.

As discussed in detail below, although the present invention finds particular utility in the context of prosthetic implants, it is readily understood that the concepts may be extended to other medical devices and biocompatible structures. In a similar fashion, although the present invention finds particular utility in the context of biological cells, such as stem, precursor and differentiated cells, as well as a wide range of graft and transplant materials, including autologous, homologous and heterologous transplant materials such as bone marrow and connective tissues, the concepts of the present invention are not limited thereto and may be readily applied to the capture of other target cells and molecules, for example pathogen cells and bioactive peptides such as growth factors.

It is a further object of the present invention to provide sterile kits and packaging systems, for example as a kit adapted for the construction of a bioactive material-immobilizing coating including:
  a. a sterile solution of a polar liquid and amphiphilic molecules, wherein the amphiphilic molecules include at least one targeting moiety having binding affinity for a bioactive material of interest, such as a target molecule or a surface moiety of a target cell; and
  b. a sterile, relatively non-polar liquid.

In addition or alternatively, the device or kit components of the present invention may be bundled in a sterile package that facilitates contact between the biocompatible device and the bioactive material of interest. For example, the package may be adapted to permit the passage of a biological fluid through an interior surface of the device.

It is yet a further object of the present invention to provide methods of making and using the components of the present invention. To that end, the present invention provides for the construction of a medical device having a bioactive material-immobilizing coating disposed thereon by:
  a. providing a biocompatible medical device;
  b. contacting the medical device with a non-polar solution to yield a medical device having a non-polar film coating disposed thereon;
  c. contacting the coated medical device of step b with an amphiphilic molecule-containing polar solution, either in conjunction with step b or after step b, to yield a medical device having a non-polar film coating disposed thereon, the film coating having a monolayer of amphiphilic molecules disposed thereon;
  d. optionally contacting the coated medical device of step c with a polar rinse solution; and
  e. exposing the coated medical device to a second polar solution containing one or more bioactive materials of interest, such as target molecules or cells to which the targeting moieties of the amphiphilic molecules have a binding affinity, to yield a medical device having a non-polar film coating disposed thereon, the film coating including said amphiphilic molecules disposed as a monolayer thereon, the amphiphilic molecules being bound to said target molecules or cells.

In a preferred embodiment, the second polar solution is or is derived from a subject-extracted tissue sample, for example a graft or transplant material including autologous, homologous and heterologous transplant materials such as bone marrow and connective tissues.

As noted above, although the present invention finds particular utility in the context of stem-cell coated prosthetic implants, it is readily understood that the concepts may be extended to other medical devices and biocompatible structures and the capture of other target cells and molecules.

In addition to serving as a substrate for bioactive material capture, the amphiphilic films of the present invention also find particular utility as coatings for porous implants. The liquid-based systems of the present invention have the unique ability to create films on otherwise inaccessible surfaces. Additionally, where films of the present invention can form non-polar-liquid-filled micelles, micelles of this type tend to break down or coalesce when introduced into a porous construct. With a low density of micelles, the films just move to the walls and coat them. With a higher density of micelles, the micelles coalesce with each other or partly with the wall, creating a more viscous fluid that effectively "clogs" the pores of the device. If bioactive material is bound to the micelles as they are introduced into the pores, the coalescence of the micelles and clogging of the pores will result in a reduction in undesirable circulation or flow of bioactive material out of the pores of the device.

In a broader sense, it is also an object of the present invention to provide a medical implant device composed of a solid porous material wherein the above-described or other biocompatible, viscous materials are utilized in certain pores of a porous device and not in other pores, in a manner that, when in vivo, permits early ingrowth of tissue into certain porous surfaces of an implant device and not others. Accordingly, a device of this design will have a first external surface and a second external surface, wherein the first external surface is coated with (also the pores of that surface have embedded within them) a biodegradable viscous or solid material that impedes flow of material across said first external surface making the second external surface the more conducive avenue for tissue ingrowth. In one preferred embodiment, a highly viscous material is embedded in a perimeter zone of the device, the first external surface, to act as a hydraulic barrier and to constrain a less viscous material, preferably a bioactive material, disposed in the center zone and in the second external surface of the device.

It is also an aspect of the present invention that viscous materials of value can also comprise emulsions and foams. An emulsion or foam that supersaturated with oxygen has the potential to expedite cell proliferation and subsequent healing as the oxygen gradually diffuses from the emulsion or foam into the surrounding tissue. Introduction into a porous prosthetic implant of an emulsion or foam where the oxygen concentration is greater than 20% of the gas present in the emulsion or foam is an aspect of the present invention.

It will be understood by those skilled in the art that one or more aspects of this invention can meet certain objectives, while one or more other aspects can meet certain other objectives. Each objective may not apply equally, in all its respects, to every aspect of this invention. As such, the preceding aspects can be viewed in the alternative with respect to any one aspect of this invention. These and other aspects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other aspects, features, benefits and advantages of the present invention will be apparent from this summary and certain embodiments described below, and will be readily apparent to those skilled in the art. Such aspects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows:

In FIG. 1a, the implant has been exposed to amphiphilic molecules with fluorescently tagged aptamers in which no non-polar liquid is present. In FIG. 1b, the metal implant is first exposed to oleic acid (an exemplary non-polar liquid) in a manner that forms a thin film on the surface before being exposed to the fluorescently tagged aptamers. As can be seen from these images, aptamers can be successfully immobilized on the surface of a metallic implant using the present invention.

In FIG. 2a, the slide has received no additional treatment or coating.

DETAILED DESCRIPTION OF THE PREFERRED EMBODIMENTS

Figures 1A, 1B:
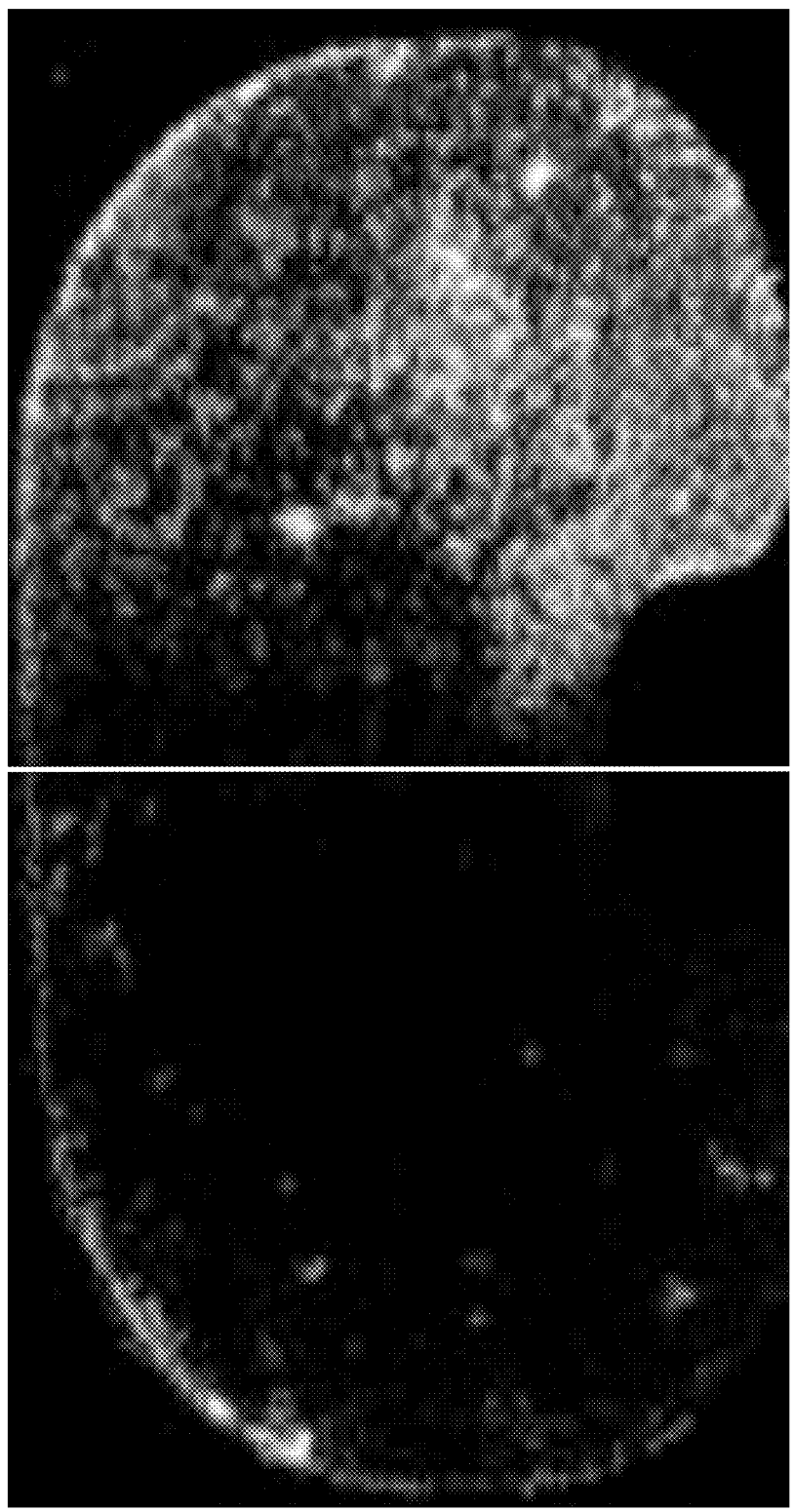
FIGS. 1a and 1b are images of tantalum metal implants photographed using a fluorescence microscope.

The present invention relates to constructs and methods for immobilizing bioactive material, including stem and other precursor cells as well as other bioactive molecules of therapeutic value, on the surface(s) of medical devices, such as bone, cartilage, spinal and tooth implants. The constructs, devices, kits and methods of present invention described herein have broad application to the incorporation and/or immobilization of bioactive material in or on a medical implant or other interventional device, having particular value in enabling the utilization by medical personnel of bioactive materials extracted from the patient and subsequently reintroduced and immobilized in an implant device. Thus, the present invention addresses a need in the art for the real-time capture and delivery of bioactive molecules and particularly the real-time utilization of extracted tissues and fluid, whether from an intended recipient or a selected donor organism, as well as materials that are synthetically produced or produced from cell cultures.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

A. Elements of the Present Invention

As used herein and in the appended claims, the singular forms "a", "an" and "the" include plural reference unless the context clearly dictates otherwise. Thus, for example, reference to a "molecule" is a reference to one or more molecules and equivalents thereof known to those skilled in the art, and so forth.

In the context of the instant invention, the terms "medical device", "implant" or "prosthesis" encompasses both devices intended for limited or temporary introduction (for example, bioerodible tissue scaffolds) as well as devices intended for long term or permanent insertion (for example, artificial bone or cartilage). As used herein and in the appended claims, the term "medical device" refers to any apparatus, appliance, instrument, implement, material, machine, contrivance, implant, in vitro reagent, or other similar or related article including a component party or accessory which is intended for the diagnosis, prevention, monitoring, treatment or alleviation of disease, injury or handicap. It further encompasses any article intended to affect the structure or function of the body of humans or other animals, and which does not achieve its principal intended action in or on the body exclusively by pharmacological, immunological or metabolic means, but which may be assisted in its function by such means. Illustrative examples of medical devices contemplated by the present invention include, but are not limited to, bone, cartilage and tooth implants (also prosthetics and substitutes), wound dressings, sutures, staples, anastomosis, vertebral disks, bone pins, suture anchors, haemostatic barriers, clamps, screws, plates, clips, vascular implants, tissue adhesives and sealants, tissue scaffolds, various types of dressings, intraluminal devices, vascular supports, and other body contacting devices that may benefit from incorporation with therapeutic materials such as therapeutic agents, bioactive molecules, and biological cells or tissues. Also contemplated are devices such as needles, catheters (e.g., intravenous, urinary, and vascular catheters), stents, shunts (e.g., hydrocephalus shunts, dialysis grafts), tubes (e.g., myringotomy tubes, tympanostomy tubes), implants (e.g., breast implants, intraocular lens), prosthetics, and artificial organs, as well as cables, leads, wires, electrodes associated therewith (e.g., leads for pace makers and implantable defibrillators, bipolar and monopolar RF electrodes, vascular guidewires), and devices for isolation and/or concentration of bioactive materials.

Certain aspects of the present invention permit incorporation of bioactive materials into the construct of a medical or surgical device construct without necessitating conjugation, also chemical bonding, with the device material and as a consequence, any biodegradable and/or biocompatible material which has value as a part of a medical device, for example a prosthetic implant construct, is of value in the present invention.

The present invention makes reference to amphiphilic molecules, particularly amphiphilic molecules that spontaneously assemble into film monolayer at the interface between a relatively non-polar material and relatively polar environment. As used herein, the term film monolayer is inclusive of any plurality of amphiphilic (also amphiphatic or surfactant) molecules aligned at the interface between a non-polar (also less-polar) liquid and polar (also more polar) liquid. Such a monolayer can be present in a wide variety of forms ranging from broken films where alignment is limited to a hydrophobic/hydrophilic alignment perpendicular to the non-polar to polar interface to more complex crystalline films and β-pleated sheets. Many of these films are known to those skilled in the field of surfactants. Monolayers of the present invention can also consist of a combination of different amphiphilic molecules. Such combinations can have value in providing a range of binding moieties to a single target cell or molecule, or in providing a film that can capture a variety of cells or molecules, particularly ones with synergistic effects. Such combinations can also provide benefit in reducing the cost of a film by achieving a dense molecule layer where only some of the molecules have an expensive binding moiety. By providing a combination of molecules in a monolayer, the strength of the film can also be increased. Typically, the monolayer at the interface is a single molecule thick, however as long as the monolayer at the interface results in an alignment of binding moieties towards the non-polar liquid, the monolayer can be more than one molecule thick and still be of value in the context of the present invention.

Amphiphilic molecules suitable for use in the context of the instant invention can either be of natural origin or can be synthetic conjugates created with specific properties. By definition, an amphiphilic molecule includes both hydrophilic and hydrophobic moieties. Whether a given amphiphilic molecule will form a stable film at the interface between a polar solution, which acts as a solvent, and a non-polar solution depends on a variety of factors, including concentration, structure of the molecule, temperature and the presence of other amphiphilic molecules which might tend to increase the film stability. Many growth factor molecules have been found to be glycoproteins and may either be amphiphilic in nature or be such that they can be conjugated with other molecules to form an amphiphilic molecule using techniques known to those skilled in the art. Illustrative methods and materials for forming such amphiphilic films are described in WO 2008/154603 (Richard Spedden), the entire contents of which are incorporated by reference herein.

The present invention makes reference to "bioactive materials" such as stem cells, other biological cells, bioactive molecules, particularly growth factors, and other materials of therapeutic value. Bioactive materials suitable for use in the context of the present invention may include, but need not be limited to, tissues or extracts thereof or other fluids extracted from the patient who is the intended recipient of the medical procedure which utilizes the resulting prosthetic device, or bioactive materials from origins other than from the patient. Forces that can impart movement of fluid and bioactive materials into an intended biocompatible construct, such as porous prosthetic device can include, but not be limited to, pressure or compressive force, gravity, centrifugal force, friction or other mechanical forces, electrical force, osmotic forces and any other force which one skilled in the art might employ.

Bone marrow for clinical use is typically obtained as an aspirate extracted from a target patient's bone using a syringe-type device. Often the iliac crest, pelvis, or pelvic bone is used as a source due to its large size and proximity to the surface of the body. In some applications, the bone marrow is used without modification, but in many cases some form of separation technology, such as centrifugation, is used to concentrate the desired fraction of the bone marrow. Stem cells and growth factors, are often the target of this separation process. Other bioactive molecules and or other cell types can also be desired targets. Cells and molecules of interest are also typically obtained from adipose, also fat, tissue. Any tissue of the body has potential, muscle and nerve tissue and tissues associated with the reproductive process are also of particular interest. Material extracted from the patient has several advantages over other sources, such as: inherent biocompatibility, potential for lower cost, providing a broader spectrum of useful compounds which might have synergistic effects and potentially reduced regulatory issues or faster regulatory approval. In current surgical practice, bone marrow derivatives are typically reintroduced into the body by injection by syringe into an area of desired activity. Often a porous retention media such as a collagen sponge is used to retain the material in the area.

The term "stem cell" represents a generic group of undifferentiated cells that possess the capacity for self-renewal while retaining varying potentials to form differentiated cells and tissues. Stem cells can be totipotent, pluripotent or multipotent. Derivative stem cells that have lost the ability to differentiate also occur and are termed 'nullipotent' stem cells. A totipotent stem cell is a cell that has the ability to form all the cells and tissues that are found in an intact organism, including the extra-embryonic tissues (i.e. the placenta). Totipotent cells comprise the very early embryo (8 cells) and have the ability to form an intact organism. A pluripotent stem cell is a cell that has the ability to form all tissues found in an intact organism although the pluripotent stem cell cannot form an intact organism. A multipotent cell has a restricted ability to form differentiated cells and tissues. Typically adult stem cells are multipotent stem cells and are the precursor stem cells or lineage restricted stem cells that have the ability to form some cells or tissues and replenish senescing or damaged cells/tissues. Further information may be found in WO 08/007,082, the contents of which are incorporated by reference herein.

The term "progenitor cell" refers to unipotent or multipotent cells, which comprise the stage of cell differentiation between stem cells and fully differentiated cells.

The term "biological cell" refers to any cell capable of performing useful biological functions in a living organism, particularly replication to form a tissue structure. The term as used herein includes stem cells, progenitor cells and fully differentiated cells. Biological cells may include cells from the intended host organism or those from a donor organism. Biological cells can include cells from recombinant or genetic engineering techniques.

The term "bioactive molecules" refers to any molecule which has the capacity to interact with a living tissue or system in such a way as to exhibit or induce a biological activity in an organism, tissue, organ or cell, either in vivo, in vitro or ex vivo.

Of particular interest in the context of the present invention are bioactive peptides that trigger or regulate biological functions. Illustrative examples of bioactive molecules suitable for use in the context of the present invention include, but are not limited to, are growth factor proteins, such as TGFβ, BMP-2, FGF and PDGF.

As used herein and in the appended claims, the term "growth factors" refers to the broad class of bioactive polypeptides which controlling and regulating a variety of endogenous biological and cellular processes, such as cell-cycle progression, cell differentiation, reproductive function, development, motility, adhesion, neuronal growth, bone morphogenesis, wound healing, immune surveillance and cell apoptosis. Growth factors typically operate by binding to specific receptor sites on the surface of target cells. Growth factors include, but are not limited to, cytokines, chemokines, polypeptide hormones and the receptor-binding antagonists thereof. Examples of well known growth factors include but are not limited to:

Bone Morphogenic Protein (BMP);
Transforming growth factor beta (TGF-β);
Interleukin-17;
Transforming growth factor alpha (TGF-α);
Cartilage oligomeric matrix protein (COMP);
Cell Density Signaling Factor (CDS);
Connective tissue growth factor (CTGF);
Epidermal growth factor (EGF);
Erythropoietin (EPO);
Fibroblast growth factor (FGF);
Glial Derived Neurotrophic Factors (GDNF);
Granulocyte-colony stimulating factor (G-CSF);
Granulocyte-macrophage colony stimulating factor (GM-CSF);
Growth differentiation factor (GDF);
Myostatin (GDF-8);
Hepatocyte growth factor (HGF];
Insulin-like growth factor (IGF);
Macrophage inhibitory cytokine-1 (MIC-1);
Placenta growth factor (PIGF);
Platelet-derived growth factor (PDGF);
Thrombocyte concentrate (PRP);
Thrombopoietin (TPO);
Vascular endothelial growth factor (VEGF);
Activin and Inhibin;
Coagulogen;
Follitropin;
Gonadotropin and Lutropin;
Mullerian Inhibiting Substance (MIS) also called: Anti-Müllerian hormone (AMH) Müllerian inhibiting factor (MIF) and Mullerian inhibiting hormone (MIH);
Nodal and Lefty; and
Noggin Molecules which regulate, induce or participate in useful biological processes in the body, including those listed above, are often categorized or classified according to their particular structure or function. For example, immunoregulatory proteins secreted by cells of the immune system, such as interleukin and interferon, are often referred to as cytokines. Other categories of regulatory molecules include, but are not limited to:

morphogens (e.g., molecules that regulate or control the formation and differentiation of tissues and organs);
chemokines (e.g., any of a group of cytokines produced by various cells, as at sites of inflammation, that stimulate chemotaxis in white blood cells such as neutrophils and T cells);
hormones (e.g., a product of living cells that circulates in body fluids such as blood and produces a specific, often stimulatory effect on the activity of cells, usually remote from its point of origin);
receptors (e.g., a molecule present on a cell surface or in the cell interior that has an affinity for a specific chemical entity, including both endogenous substances such as hormones and ligands as well as foreign materials, such as viral particles, that serves as an intermediary between the stimulating agent and the downstream physiological or pharmacological response thereto;

receptor-binding agonists (e.g., a chemical substance capable of combining with a specific receptor on a cell and initiating the same reaction or activity typically produced by the endogenous binding substance (such as a hormone); and receptor-binding antagonists (e.g., a chemical substance that reduces the physiological activity of another chemical substance (such as a hormone) by combining with and blocking one or more receptors associated therewith).

However, since the study of the function of the various regulating moieties in the body is still an emerging science, the categorization thereof is also evolving. Accordingly, the present invention is not limited to any one particular class or category of regulating or stimulating molecules.

As used herein and in the appended claims, the term "growth factors" also refers to precursor forms of growth factors, which are typically inactive until they undergo endoproteolytic cleavage, as well as synthesized and recombinant forms which provide part or all of the same or similar functions as the naturally occurring growth factors. Accordingly, the present invention encompasses precursors, analogues, and functional equivalents of growth factors, provided the resulting molecules retain some or all of the function of regulating useful biological processes in the body, typically by binding to specific receptor sites on the surface of target cells associated with the wild-type or endogenous moiety.

The term "therapeutic agents" as used herein refers to any molecule, compound or composition having therapeutic potential, more particularly pharmaceutical activity. Examples of particularly useful therapeutic and/or pharmaceutical activities include but are not limited to anti-coagulation activity, anti-adhesive activity, anti-microbial activity, anti-proliferative activity, and biomimetic activity.

The term "antimicrobial" refers to any molecule which has the capacity to limit or interfere with the biological function of a bacterial, fungal or viral pathogen or a toxin. Antimicrobial is intended to also encompass antibacterial, antibiotics, antiseptics, disinfectants and combinations thereof.

The term "therapeutic materials" refers to any composition which comprises any of the following: therapeutic agents, bioactive molecules, stem cells, progenitor cells or biological cells. The term "bioactive solution" refers to a liquid composition which comprises, in part, bioactive materials.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents.

As used herein, the term "bone" refers to the rigid organs that form part of the endoskeleton of vertebrates and function to move, support, and protect the various organs of the body, produce red and white blood cells and store minerals. One of the types of tissues that make up bone is the mineralized osseous tissue, also called bone tissue, which gives it rigidity and honeycomb-like three-dimensional internal structure. Other types of tissue found in bones include marrow, endosteum, and periosteum, nerves, blood vessels and cartilage.

Accordingly, the term "tissue" as used herein broadly encompasses all biological components including, but not limited to, skin, muscle, nerves, blood, bone, cartilage, tendons, ligaments, and organs composed of or containing same.

In the context of the present invention, the term "isolated", as in, for example 'isolated from biological tissues or cells', refers to any process which separates the therapeutic material of interest from the tissue or cell membranes in a manner which preserves the structure and function of therapeutic material of interest. The term "isolated" as used herein is synonymous with the terms "extracted" and "harvested", for example.

In addition to being isolated, harvested or extracted from natural sources, therapeutic materials suitable for use in the instant invention can also be "derived from" biological sources, for example, synthetically produced or produced by genetically engineered plants and animals, including bacteria and other microbes, in accordance with well-known and conventional techniques.

As used herein and in the appended claims, the term "non-polar" refers to a substance or mixture of substances that is relatively uncharged when compared to a polar solvent being used. The concept is also reflected in the references herein to systems of "differing" or "diverging" polarity. As such, the terms "relatively non-polar" "less-polar" can be interchangeably exchanged herein for the term "non-polar". The non-polar material is typically water insoluble (hydrophobic). A mixture of non-polar and polar substances can be used to form the non-polar material of this invention as long as the resulting combination supports the formation of an amphiphilic film when in the presence of a selected polar solvent. It is further an aspect of the present invention that the non-polar liquid can be of a nature where it can transition to a solid film as taught by Spedden in WO 2008/154603 referenced above, the entire contents of which are included herein by reference.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

B. Illustrative Embodiments of the Present Invention

It is an object of the present invention to provide materials and methods which permit a medical device to be exposed to a liquid system, prior to or during surgery, that forms a thin film on the exposed surfaces, and that such a film contains moieties or molecules having selective binding affinity for one or more types of biological cells or other bioactive material. In a preferred embodiment, the target bioactive material is stem cells, due to their broad therapeutic benefits. However, more differentiated cells and other bioactive molecules of therapeutic interest may also be targeted. Furthermore, the device of interest can be exposed to fluids containing such cells or material either prior to or after introduction of the device in the body. In a preferred embodiment, a bone marrow aspirate or other autologous stem cell-bearing fluid is used. However, other fluids, particularly custom designed compositions with commercially available cells or molecules can also be of value.

To achieve this end, the present invention envisions the use of amphiphilic molecules wherein the hydrophilic end exhibit specific binding affinity for a targeted cell or bioactive molecule. Further, in the context of the present invention, the molecules with the targeting moieties are, either alone or in combination with other amphiphilic molecules, allowed to form an amphiphilic monolayer film at the interface between a non-polar (or relatively less-polar) liquid and a polar liquid, such that the targeting moieties are expressed on the polar liquid side of the film. Non-polar liquids, typically oils, are known to readily form thin films on many solid surfaces, such as are encountered in medical implant devices. An amphiphilic film is typically a single molecule thick (i.e., a monolayer) and tends to stabilize the interface between a non-polar liquid and a polar liquid. These properties make such a system ideal for medical implant surfaces, particularly the internal surfaces of a porous device, such as a Trabecular Metal™ implant or a woven or other filamentous scaffold. Water, saline solution and most bodily fluids constitute appropriate polar liquids to allow an amphiphilic film to form and be sustained.

Many non-polar liquids, such as oils, are currently used in medical applications. In the preferred embodiment, a fatty acid such as oleic acid is used. Other non-polar materials, such as various oils, silicone and glycerin, can also be readily used. Biocompatibility is a desirable property, since eventually the film may breakdown. Though, the fact that only a very thin film of the selected non-polar material is required and the fact that the amphiphilic film at the interface between polar and non-polar liquids insulates the selected non-polar material from direct contact with bodily fluids reduces the possibility or degree of any immunological reactions to the non-polar liquid.

Amphiphilic molecules of the present invention are typically a conjugation of one or more molecules forming a hydrophobic tail, an optional spacer molecule and one or more molecules forming a hydrophilic head with desired binding moieties. In a preferred embodiment, the hydrophobic tail is composed of a hydrocarbon chain of the form $(CH_2)_n$, where "n" represents the number of hydrocarbon groups and is typically 12 or greater. Lipids and other inorganic and organic molecules can exhibit appropriate hydrophobic properties. Glycolipids, phospholipids and glycoproteins are in many instances amphiphilic by nature and depending on length and structure, may or may not be suitable for forming appropriate films. Synthetic polymers, such as polyethylene glycol (PEG), are often used in the formation of biocompatible, amphiphilic molecules. In US Patent Publication 2007/0141134, Kosak teaches the use of PEG conjugated to aptamers in the formation of micelles used as molecular delivery vehicles. The techniques taught in the formation of these amphiphilic molecules can be used to generate materials of use in certain aspects of the present invention.

The binding moiety can be any molecular sequence that exhibits the necessary specificity for the targeted cell or molecule. In the preferred embodiment, the binding moiety is a nucleic acid targeting moiety (most preferably an aptamer), where the aptamer has been selected because of a specific binding affinity for a therapeutic cell or molecule, most preferably a stem cell or other precursor cell. Antibodies and products of phage-display techniques are also of value in providing the target specific moieties in constructs of the present invention. Other molecules with known binding affinities may also be used, though often these do not exhibit as high a degree of specificity. P-selectin, for example, exhibits useful binding moieties for stem cells.

Aptamers are macromolecules composed of nucleic acid that bind tightly to a specific molecular target that can be economically produced in volume. Tuerk and Gold (Science. 249:505-510 (1990)) disclose the SELEX (Systematic Evolution of Ligands by Exponential Enrichment) method for selection of aptamers. In the SELEX method, a large library of nucleic acid molecules {e.g., $10^{15}$ different molecules) can be used for screening. A desired molecular sequence can be identified through the use of the technology of systematic evolution of ligands by exponential enrichment (SELEX). Aptamers are currently used in a range of biotechnological and therapeutic applications. They are a competing technology to more costly antibodies and have specific advantages over antibodies since they are produced by chemical synthesis (reducing the cost), can be stored and transported easily and have been shown to elicit little or no immunogenicity in therapeutic applications.

Due to the self-aligning nature of an amphiphilic film, binding moieties presented on the hydrophilic heads of the amphiphilic molecules are exhibited at an extremely high density on the polar liquid side of the film. It is an aspect of the present invention that the density of any specific binding moiety in the surface can be controlled by the introduction of other amphiphilic molecules into the polar solution prior to formation of the film. To form a film with the highest density of binding moieties possible, only amphiphilic molecules with a specific binding moiety present are introduced. However, the polar solution can also be a mixture of amphiphilic molecules with binding moieties and other amphiphilic molecules that do not exhibit binding moieties. Additionally, different amphiphilic molecules can possess different binding moieties. The aptamers in a mixture can target a range of different cell types or molecules. It is an aspect of the present invention that a number of different aptamers with moieties targeting different features on the same type of cells can be used in a single mixture to increase the chance of binding those target cells.

In another embodiment, the present invention takes the form of a kit composed of precursor components of the present invention and a method of using the same. In its simplest form, a non-polar liquid is allowed to coat the surfaces of a medical implant or other device. If the surface has hydrophobic characteristics, the non-polar liquid will spread to form a very thin film on the surface. Excess non-polar liquid can be allowed to drain or be flushed from the device. The medical device surfaces are then exposed to a polar solution containing the amphiphilic molecules with nucleic acid binding moieties expressed on the hydrophilic head of the molecules. Typically, excess amphiphilic molecule bearing polar solution is drained or flushed from the device so as to reduce the chance of target molecules or cells binding to amphiphilic molecules which are not embedded in surface films. To maintain stability of the amphiphilic film, it is preferred that the surfaces maintain a coating of polar liquid (also, remain wet). In the preferred embodiment, the device would either be immediately implanted in a patient or exposed to fluids from the patient or a surrogate, or otherwise stored in a polar solution, such as a sterile saline solution.

In another embodiment, present invention contemplates micelle-like structures surrounding a non-polar liquid core formed utilizing amphiphilic (also bioactive) films such as those described above for medical device surface coatings. As with those films described above, the film can be formed either of molecules exhibiting binding moieties to cells or therapeutic molecules of interest, or of molecules that actually incorporate therapeutic molecules in the hydrophilic head of the amphiphilic molecule. Further, the non-polar liquid cores in such structures can contain additional therapeutic materials.

In another embodiment, the present invention contemplates a solution containing the above micelle, or micelle-like constructs, in which the non-polar liquid is encased in the bioactive film, and its use in connection with a porous medical implant device wherein the micelles migrate into pores of the device. Liquid core micelles often tend to coalesce over time. These micelles can also be induced to coalesce due to environmental factors such as increased temperature, mechanical action or changes in pH. The coalescing of the micelles in the confined space of a pore can increase the interaction between the micelle constructs and the pore wall, with the result of increased friction that can result in the construct being immobilized in the pore. The same effect can be achieved if the micelle construct fails and the pore wall becomes part of the micelle boundary (think of a soap bubble sitting on the surface of water in the form of half a sphere). In some cases where the liquid core micelle fails when in contact with the implant surface, the non-polar liquid will distribute as a thin film on the implant surface with the amphiphilic film realigning as a barrier between the thin film of non-polar liquid on the implant surface and the surrounding polar liquid, thus forming a construct described elsewhere.

These effects, which tend to immobilize the films and the non-polar liquid, are of value in the context of the present invention as a means of introducing and then immobilizing bioactive materials within the pores of the prosthesis. Once implanted in the patient, the biological processes of the body gradually induce the release the bioactive materials. Such biological processes include both processes that react with and remove bioactive molecules from the films, as well as enzymatic and other processes that might interact with oils or other non-polar materials in the constructs.

An important additional feature of the constructs of the present invention, particularly those embodiments wherein micelles coalesce in the pores, is that the film structures not only immobilize the amphiphilic bioactive molecules and the non-polar liquids in the pores, but they also block circulation of polar liquids in the pores, effectively trapping pockets of polar liquids and any materials contained there-in. This represents an additional aspect of the present invention. The polar liquids can contain bioactive molecules as well as biological cells. Thus water soluble bioactive molecules, which are not necessarily amphiphilic in nature, can be effectively immobilized in the resulting pockets of polar liquid. Additionally, these pockets can contain biological cells, and of particular value stem and/or precursor cells.

In addition to micelle-like structures, the films can be contained in oil-in-water or water-in-oil emulsions, both of which are of value in the context of the present invention. Such emulsions tend to be viscous in nature; they flow under pressure and consequently can be pumped, injected or otherwise introduced into a porous prosthesis, but once there, viscous forces will tend to hold the emulsions in place. The benefits of these constructs will be the same as those stated for the micelle structures once they are embedded in the pores of the prosthesis.

A suitable non-polar liquid can be chosen on the basis of physical properties, such as viscosity, or bio-absorption properties or on any other basis that achieves the desired results. The non-polar liquid can also provide therapeutic properties; for example, fatty acids are known to have some antimicrobial properties, non-polar liquids can be used as carriers for hydrophobic materials, and oils such as oleic acid are thought to have synergistic effects in combination with growth factors in stimulating stem cell differentiation and growth. The use of oleic acid and other fatty acids is particularly preferred in the present invention.

In another embodiment, the present invention takes the form of a gas-liquid foam (also mixture) construct. Such constructs can also be viscous in nature. Due to surface tension properties, the viscous effects are more pronounced with increased interaction with the surrounding walls, as in small pores. Consequently, as with emulsions, the foams can be introduced into a porous prosthesis under pressure and then once in place the viscous forces will tend to immobilize the material in the pores until biological processes gradually break down the foam. As with emulsions, the polar liquid that is entrapped in the pores by the foam can contain bioactive molecules and biological cells of therapeutic value. In the case of foam used in vivo, the type and quantity of gas is important. In most embodiments of the present invention, oxygen will be the preferred gas. Oxygen has the important characteristics of not only being readily absorbed by surrounding tissue, but also being of known value in the promotion of rapid formation of tissue. In excess quantities, oxygen can also serve as an antibiologic. Antibiologic properties can be of value when utilized to combat infections, which are an issue with any prosthetic implant. Though the antibiologic properties can also hinder tissue development if the gas quantity and diffusion rate is not kept to an acceptable level. The appropriate oxygen concentration will differ according to application. Tissue oxygen concentrations can range from hypoxic, to normoxic, to hyperoxic at normal atmospheric pressures and are typically referenced by oxygen tension. A study by Stuart, et al., suggests that normalized oxygen tensions that are twice the normoxic level are optimum for angiogenesis.[1] Any levels above hypoxic are beneficial in modulating bacterial growth. In the context of the present invention, the oxygen in a foam or otherwise present in a material constrained in the pores of a porous medical implant will, over time, migrate into the surrounding tissue at a rate controlled both by the diffusion characteristics of the foam or other material and by the partial pressure of oxygen in the surrounding tissue. The net result is an object of the present invention wherein, prior to tissue ingrowth, the pores of the implant will have high oxygen concentrations, with inherent antimicrobial benefits, and as the oxygen diffuses out of the pores, the interface at points of tissue ingrowth will have an elevated oxygen concentration, promoting accelerated tissue growth at those points. Zheng et al. (U.S. Pat. No. 5,438,041, incorporated by reference herein) describe biocompatible emulsions with a high oxygen concentration that are applicable to the in formation of constructs of the present invention.

[1]Schugart, Richard C., Avner Friedman, Rui Zhao, and Chandan K. Sen, Wound angiogenesis as a function of tissue oxygen tension: A mathematical model, PNAS, Feb. 19, 2008, vol. 105, no. 7, 2628-2633.

In yet another embodiment, the present invention contemplates embedding two or more different materials with different viscosities in different sections of a porous medical implant (also prosthesis) to achieve a variety of effects of value in the context of the present invention. For example, a highly viscous material may be embedded in the perimeter zone of a porous material to act as a hydraulic barrier and constrain a less viscous material to remain in the center zone of a porous material. Taking a kitchen sponge that has been saturated with water and then coating it with grease can illustrate this effect, such that the grease enters the pores on the perimeter of the sponge. The grease will tend to block the water from draining out of the sponge. The same effect can be achieved using a porous medical implant, any highly viscous, biocompatible material and a less-viscous liquid with bioactive molecules and/or biological cells. In a preferred embodiment, the two or more materials with different viscosities are biodegradable or bio-absorbable, though potentially at different rates. In this manner, bioactive molecules or biological cells contained in any or all of the materials are gradually released into the area of desired therapeutic effect.

In a particularly preferred embodiment, the highly viscous material on the perimeter of the medical implant includes antimicrobial materials. This provides an important benefit in combating infection that may have been introduced into the patient on the surface of the implant. The initial concentration of antimicrobial materials diffusing from the surface of the devices will gradually be replaced by the bioactive/therapeutic materials contained in the material in the interior of the device.

When porous medical implants are introduced into a patient, typically one or more surfaces function as interfaces with adjoining tissue, such as bone, with the intent that the tissue will grow into the pores of the device along that face or faces, the mating face(s). Accordingly, the present invention contemplates that the mating face(s) can have embedded in the pores a viscous material which either contains bioactive molecules or serves as a hydraulic barrier to prevent premature flow of less viscous material in the center of the implant and the other surfaces of the device can have embedded in the pores a material which also serves as a hydraulic barrier to the less viscous material in the center of the implant, but which either has a slower absorption rate than the materials on the mating face(s) or contains the same type of material but to a deeper depth into the device. The intent of this type of construct is to permit the therapeutic material in the center of the device to have preferential access to the mating face(s) where initial tissue growth is desired.

In a preferred embodiment of the above face specific construct, the surfaces of the implant device which are not mating face(s) can have embedded within the pores a solid material with is biodegradable or bio-absorbable. Examples or such materials include, but are not limited to, PLA, PEG and bio-absorbable waxes. Biodegradable PLA and PEG compositions, with and without bioactive peptides are known to those skilled in the art. An example of a bio-absorbable wax of value in the present invention is taught by Nathan, et al., in U.S. Pat. No. 7,030,127, "Composition and Medical Devices Utilizing Bioabsorbable Polymeric Waxes", the entire contents of which are included herein by reference.

The embodiments described herein are well suited to the use of patient-derived materials, such as bone marrow or adipose tissue extracts. Such extracts can be injected directly into the hydraulically isolated center of a porous implant, or, alternatively, the materials can be compounded with non-polar materials to make micelle or emulsion constructs that may be more readily immobilized in the pore structure due to viscous forces.

Accordingly, a porous implant device can be coated or otherwise surface pore impregnated with a high viscosity, non-water soluble material to form a hydraulic barrier. A portion of one or more surfaces can be left uncoated so as to permit introduction of a lower viscosity material to fill the interior voids of the device with therapeutic materials.

In another embodiment, the present invention relates to medical implant devices incorporating the concepts of the present invention, wherein such devices are provided in a sterile package, or placed in a separate device that permits biological fluids to be passed through the device. Illustrative examples of such devices that may be adapted for use with the constructs and devices of the instant invention are described in related co-pending U.S. patent application Ser. No. 12/498, 557, the contents of which are incorporated by reference herein. Accordingly, the process of passing a fluid carrying endogenous material through a porous implant device, before, during or after the device is implanted in the patient is considered to be an aspect of the present invention. To that end, the present invention contemplates the use of external equipment or structure in which the implant device is held, where there is a hydraulic seal to or surrounding the structure to insure passage of fluid through the implant, and with one or more hydraulic connections for introduction of endogenous or other biologic material and one or more connections hydraulic connections for removal of material.

In another embodiment, the present invention provides materials and methods enabling therapeutic materials, including, but not limited to, therapeutic agents such as antimicrobials (also antibiotics, antiseptics, disinfectants and combinations thereof), bioactive materials, including but not limited to growth factors and other bioactive molecules, and biological materials such as stem cells, progenitor cells and other biological cells to be delivered to a site of desired therapeutic use, such as for tissue repair or wound healing. Though not intended as limiting to the application, the materials and methods of the present invention find particular utility in the context of surgical procedures, enabling medical personnel to utilize therapeutic materials that may require immediate use or have restrictive storage requirements, for example stem cells. The present invention also allows therapeutic materials derived from a patient to be used in a therapeutic manner on that same patient, thus reducing the possibilities of adverse reactions.

In yet a further embodiment, the present invention provides a kit composed of i) a sterile package, or one that can be sterilized, said sterile package containing ii) one or more porous prosthetic medical devices, such devices optionally composed, in part, of surfaces disposed with surface molecules or non-polar films which represent potential binding sites for bioactive molecules, the binding sites based on potential bonding through chemical conjugation, absorption and/or hydrophobic interaction or other mechanisms for bonding bioactive materials to substrate materials which are known to those skilled in the art. Furthermore, the kit can provide for introduction into the sterile package (e.g., via ports) of target agents comprising bioactive molecules, cells, other therapeutic or antimicrobial materials or protective or otherwise useful materials, including, but not limited to, flushing agents, binding agents or coating agents, and that these provisions find particular value when configured to permit medical personnel to introduce into the package material extracted from the prospective patient which are thought to include bioactive molecules or cells. Illustrative for introducing target agents include, but need not be limited to, areas for injection of, or otherwise introduction of, fluids or other materials into the sterile package where the package is then reseal-able or self-sealing, as might be envisioned by those skilled in the art. The kit may optionally further provide for the removal from the package of excess target agent(s), e.g. via ports, and can include, but need not be limited to, areas for extraction using hypodermic needles, one-way valves, deformable polymers which separate and allow flow out when sufficient pressure is exerted on the package, or other directional flow limiting, reseal-able or self-sealing devices as may be envisioned by one skilled in the art. A properly designed port, can in certain aspects of the present invention serve as both a port for introduction of material as well as a port for removal of material. In other cases of the present invention, there may be advantages to a package having a proximal end and a distal end, such that the introduction port is located at the proximal end of the package and the discharge port is located at the distal end of the package. This dual port package provides the advantages of a flow through design that assures that the target agent(s) is well distributed in the package and consequently has an increased probability of contact with all relevant portions of the device.

In yet a further embodiment, the present invention provides for the construction and method of use of a kit configured to permit one or more target agents, including, but not limited to, antimicrobial molecules and/or hydrophobic coating molecules, for example fatty acids, the first agent(s), to be applied to a portion of the medical device of interest and then permit in a subsequent step the coating or otherwise covering of the portion with an additional target agent or agent(s), the second agent(s), including, but not limited to antimicrobial molecules and/or hydrophobic coating molecules, for example fatty acids, or other therapeutic or protective coatings, in a manner where upon removal of the device from the package, the assembled medical device exhibits certain surface properties of protective or therapeutic use associated with the second agent(s) while the interior of the device exhibits additional or other properties of therapeutic use related to the first agents(s). The kit can include any configuration known to those skilled in the art for sequential application of material, including, but not limited to i) sequential introduction of material in one package zone, and ii) passage of the device through two or more package zones where different materials can be applied prior to or during removal of the device from the package. In the case of a package with two or more zones for application of target agents, in certain aspects of the present invention, each zone may have agent introduction or removal ports.

The present invention further contemplates methods for applying a target agent to a portion of a medical device and subsequently coating or covering the portion with other agents or materials, such a method comprising the following steps:
  i) providing a prepared medical device in a sterile package having a port for allowing sterile passage of at least one target agent to the device;
  ii) optionally introducing a binding agent to facilitate binding of a target agent to the medical device and optionally inducing excess binding agent to be expelled from the package through a port;
  iii) introducing a target agent into the package through a port to interact with the prepared medical device;
  iv) inducing a portion of the target agent that fails to bind to the medical device to be expelled from the package through a port;
  v) optionally introducing a flushing material into the package to assist in diluting and removing excess target agent and subsequently inducing the flushing material to be expelled from the package through a port;
  vi) introducing an additional target agent, agents or coating molecules into the package through a port or otherwise cause an additional target agent, agents or coating molecules to be released in the package in a manner which results in the agents or molecules coating the medical device.

A package suitable for the application of multiple target agents to a medical device, operable according to the method described above, may include:
  i) a container for receiving the device;
  ii) a port in communication with the container for allowing sterile passage of a least one target agent, the first agent(s), to the prepared device;
  iii) a second container within the package construct comprising an additional target agent or agents (including, but not limited to antimicrobial molecules and hydrophobic coating molecules), such that the second container can be induced by external stimulus to release the additional target agents into contact with the medical device, thus permitting a medical device which has been exposed to the first agent(s) to be subsequently exposed to or coated by the second agent(s).

The present invention contemplates the use of bioactive-molecule-binding amphiphilic moieties, such as those described by Stupp et al. in US Patent Publication 2005/0209145, introducing such moieties into tissues and their derivatives extracted from a prospective patient (or intended recipient), or allografts or xenografts of the same, optionally concentrating the tissue solution before or after addition of the amphiphilic moieties, allowing conjugation of bioactive molecules present in the tissue with the binding moieties taught by Stupp, allowing the nanowires to form and entangle to form a hydrogel with viscous properties and then introducing the construct into a porous prosthetic device. The resulting construct of nanowire-based hydrogel in a porous prosthetic implant is also an aspect of the present invention, with particular value in constructs incorporating endogenous materials either bound to or embedded in the hydrogel matrix.

It is further an aspect of the present invention that any or all of the constructs described as aspects of the present invention can consist of materials mentioned for similar use in the referenced patents, the entire contents of which have been included herein by reference.

C. Methods of Making and Using Embodiments of the Present Invention:

It is an object of the present invention to provide a medical device construct adapted to incorporate materials extracted from a patient who is the intended recipient of the medical procedure, and that such extract materials can include, but need not be limited to, bioactive molecules and stem, progenitor and other biological cells. It is further object of the present invention that the therapeutic molecules and stem, progenitor and other cells be derived from any tissue of the body in which the material is present, including, but not limited to, bone marrow, adipose tissue, muscle tissue and nerve tissue and any fluids associated with those tissues. It is further object of the present invention that the medical device be adapted to incorporate materials derived from allografts, xenografts (also zenografts), or synthetic mimics of tissues of the patient who is the intended recipient of the medical procedure, and that the materials can include bioactive molecules and stem, progenitor and other cells. It is yet another object of the present invention that molecules and cells of interest suitable for use in the context of the present invention be derived from products of the human reproductive system, including autografts, allografts and xenografts of the same.

Due to surface tension and hydrophobic forces, a non-polar (or less-polar) liquid will bind to and distribute across the surface of a hydrophobic solid, and this phenomena will be strengthened by the presence of a surrounding polar liquid. The forces are such that when appropriate quantities of non-polar liquid are used, the film can be as thin as a single molecule (e.g., a monolayer). Thus, in the context of the present invention, a medical device with hydrophobic surfaces, and further provided with a non-polar (or less-polar) liquid film on such surfaces, can be exposed to a polar solution in the presence of appropriate amphiphilic molecules, at which point such amphiphilic molecules will automatically self-align at the interface between the non-polar liquid and polar solution. If sufficient amphiphilic molecules are present, a very closely pack film will develop. "Sufficient" in this case is analogous to the Critical Micelle Concentration (CMC) which determines whether micelles will form in a polar liquid with amphiphilic molecules. The CMC is dependent on many factors, including the nature of the amphiphilic molecules, the polar nature of the solvent solution, the temperature and whether other contaminants or agents are present. The same is true for forming self-assembled films on surfaces.

The non-polar (or less-polar) liquids used in the present invention are preferably biocompatible, more preferably materials which are normally present in a prospective patient's body, or analogues, homologues or functional equivalents of the materials. Examples of such materials can include, but need not be limited to, fats and oils, for example, oleic acid. The use of fatty acids, and particularly oleic acid, as the non-polar liquid of interest is preferred in the context of present invention due to its inherent biocompatibility and the potential synergy between polyunsaturated fatty acids (PUFA), and specifically oleic acid and bone morphogenetic protein (BMP-2).[2]

[2] Ryota Deshimaru, Ken Ishitani, Kazuya Makita, Fumi Horiguchi and Shiro Nozawa, Analysis of fatty acid composition in human bone marrow aspirates, The Keio Journal of Medicine, 54:3-2005, 150-155

Likewise, the amphiphilic molecules used in the present invention are preferably biocompatible and more preferably include bioactive molecules derived from a prospective patient. Other amphiphilic molecules which add to the stability of the film or provide binding moieties to other cells or bioactive molecules can be introduced. Molecules which provide binding moieties to bioactive molecules can include, among others, heparin and its derivatives and conjugates. Molecules which provide binding moieties to bioactive molecules can include the products of phage display techniques and antibodies.

The binding of members of the TGF-β cytokine superfamily (growth factors) to heparin and heparin sulphate containing molecules is known.[3] In U.S. Pat. No. 6,921,811, the entire contents of which are included herein by reference, Zomora, et al., teach the coating of medical devices with a silyl-heparin complex and a bioactive molecule directly bound to the heparin-activity molecule. In the Zomora patent, the silyl-heparin complex adheres to the medical device through hydrophobic bonding interaction. Creation of amphiphilic molecules and self-assembled films containing growth factors as taught by Zomora, can find utility in certain aspects of the novel constructs of the current invention that utilize self-assembled films.

[3] C. C. Rider, Heparin/heparin sulphate binding in the TGF-b cytokine superfamily, Biochem. Soc. Trans. (2006) 34, (458-460) (Printed in Great Britain)

In US Patent Publication 2005/0209145, the entire contents of which are incorporated herein by reference, Stupp, et al., teach the creation of amphiphilic peptide compounds that incorporate the growth factor recognition product of a phage display process and the binding of those compounds to targeted growth factors. Stupp, et al. also teach the use of these compounds in the creation of self assembled nanofibers or micelles. Certain of the techniques described by Stupp et al. may find utility in connection with the immobilization bioactive molecules in constructs of the present invention.

Discher, et al., teach the creation and use of polymersomes and related encapsulating membranes in U.S. Pat. Nos. 6,835, 394, 7,217,427 and US Patent Publications 2006/0165810 and 2007/0218123, the entire contents of all of which are incorporated herein by reference. The techniques described by Discher may find utility in connection with the immobilization bioactive molecules in constructs of the present invention.

Bhaskaran, et al. in U.S. Patent Publication 2008/0058246, the entire contents of which are incorporated herein by reference, teaches methods of synthesizing polymer conjugates of growth factor proteins and other compounds while maintaining a high level of functionality of these biological compounds. These techniques may find utility in the context of the present invention, particularly as a means to immobilize bioactive molecules in constructs of the present invention.

The constructs or methods of conjugating materials can be of value in certain aspects of the present invention, including, but not limited to the creation of amphiphilic molecules with bioactive components, which are suited to formation of films at the interface of a polar and a less-polar solution.

Alkan-Onyuksel, et al., teach the creation of micelles and crystalline products which incorporate a biologically active amphiphilic (also, amphipathic) compound in U.S. Pat. No. 6,322,810, the entire contents of which are incorporated herein by reference. The methods described in the Alkan-Onyuksel patent may be applicable to certain aspects of the present invention.

The use of HBPA-1 heparin gels (heparin and heparin sulphate) to improve angiogenesis is known and is of value in certain aspects of the present invention. These heparin gels are thought to recruit and activate endogenous growth factors present at a wound site.[4] The use of heparin and heparin sulphate in connection with the constructs of the present invention is also an aspect of the present invention.

[4] Corral, Claudio J. MD; Aamir Siddiqui, MD; Liancun Wu, MD; Catherine L. Farrell, PhD; David Lyons, PhD; Thomas A. Mustoe, MD, Vascular Endothelial Growth Factor Is More Important Than Basic Fibroblastic Growth Factor During Ischemic Wound Healing, Arch Surg. 1999; 134:200-205.

In US Patent Publications 2007/0170080 and 2008/0128296, the entire contents of both of which are incorporated herein by reference, Stopek, et al., teach the construct of a medical device package comprising a sealable pouch with a sealed port for introduction of at least one agent to the medical device contained therein. The constructs described by Stopek may find utility in connection with certain aspects of the present invention. Additionally, the present invention provides for improvements on the medical device package systems.

In certain aspects of the present invention, the viscosity of a non-polar liquid, or the emulsion or foam thereof, is an important factor in limiting the premature migration of a therapeutic from a desired area of retention. Common means of increasing the viscosity of non-polar liquids include, but are not limited to, addition of solid, and particularly fibrous, components, gelling of typically oils with components such as pectin, gelatin or aluminum salts of fatty acids such as aluminum monostearate or distearate, hydrogenation of oils, such as fatty acids, and variation of ratios of components in emulsions and foams. All of these techniques are of value in the context of the present invention. As used herein, the term "foam" refers to any mixture of gas and liquid wherein both are present in the matrix, and more typically where the gas is present as discrete zones surrounded by liquids; the presence of a surfactant is not a necessity to form a foam in the present context.

In WO/2005/053767, directed to "CIS-Hydrogenated Fatty Acid Coating of Medical Devices" the entire contents of which are incorporated by reference herein, De Scheerder, et al. teach the use of hydrogenated fatty acids as a viscous delivery mechanism for therapeutic agents when applied to medical devices, and in particular stents. The materials taught by Scheerder, et al. find value in certain aspects of the present invention. Of particular value in the context of the present invention is the ability to form materials of differing viscosities.

Stem cells and other precursor cells are known to exhibit a certain degree of stickiness to other materials. The phenomena of stem cells sticking to the surface of a polystyrene Petri dish is well known to those practiced in the art. Other molecules are known to bind stem cells and have been demonstrated as effective means for selectively removing stem cells from biological fluid.[5] In work done at MIT and the University of Rochester, P-selectin, which exhibits stem cell binding, was immobilized in a polyethylene glycol surface to form a surface which can selectively capture stem cells and, particularly in their case, cancer cells.[6] P-selectin is can be immobilized on biotinylated surfaces, such as biotinylated PEG. P-Selectin is an integral transmembrane glycoprotein expressed in endothelial cells and platelets. As a transmembrane glycoprotein, it also exhibits amphiphilic characteristics which make it suited to immobilization at the interface between polar and less-polar surfaces (the technology referenced earlier).

[5]King, Michael, Nichola Charles, Jared Kanofsky, and Jane L. Liesveld, "Using Protein-Functionalized Microchannels for Stem Cell Separation," Paper No. ICNMM2006-96228, Proceedings of the ASME, June 2006.
[6]Dougherty, Elizabeth, MIT works toward novel therapeutic device, Tech Talk, Harvard-MIT Division of Health Sciences Volume 52, Number 6, Oct. 24, 2007

P-selectin enhanced surface technology and other surface technologies which demonstrate increased binding affinity for stem cells are of value in the context of the present invention as a coating for the pore surfaces of a prosthetic implant device. Such a construct has particular utility in the present invention in the ability to selectively capture stem cells and other precursor cells from bone marrow and other bodily fluids which may be passed through the device either prior to or after introduction of the device into the patient's body. This process will result in an increased density of stem and precursor cells populating the porous implant with an increased potential for rapid growth of tissue and integration of the implant with adjacent tissues.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Generation of DNA Aptamers Having an Affinity for Human Mesenchymal Stem Cells (hMSCs)

The surfaces of human mesenchymal stem cells (hMSCs) were targeted for DNA aptamer development. The initial aptamer pool used consisted of 2 nmols of random 40-base sequences flanked on either side by known 19-base primer sequences (i.e. 5'-forwardprimer-N40-reverseprimer-3'). Reactions and incubations occurred in a selection buffer containing 50 mM Tris-HCl (pH ~7.4), 5 mM KCl, 100 mM NaCl, 1 mM MgCl2, and 0.1% NaN3. These sequences were denatured and renatured by heating to 80 C for 10 mins, cooling to 4 C for 10 mins, and then warming to room temperature for 20 mins to ensure proper binding structure. Five-fold molar excesses of both yeast tRNA and Bovine Serum Albumin (BSA) were added during the folding process to lower instances of background binding. The aptamer pool was then incubated in a 1.5 mL low-binding microcentrifuge tube with a suspension of ~1 million hMSCs (Passage 2) at 37 C and 5% CO2 for 30 mins, before being centrifuged for 10 mins at 1,500 RPMs. The aspirate, which contained non-binding aptameric sequences, was discarded, and the pellet resuspended in selection buffer with 0.2% BSA and transferred to a new microcentrifuge tube. This was repeated several times, and then the remaining sequences bound to the surfaces of the cells were amplified via polymerase chain reaction (PCR). Forward primers were FITC-tagged and reverse primers were biotinylated to assist purification and analysis. The FITC and the biotin tags were placed on the 5' end of the molecule, distanced from the nucleotides via a 9-Carbon and an 18-Carbon spacer respectively to prevent steric interference with the DNA polymerase during PCRs. Post PCR, the mixture was incubated with streptavidin-coated magnetic beads (Dynabeads® M-280 Streptavidin by Invitrogen) to remove biotinylated aptamers from the pool; these were then amplified a second time by PCR and used as the aptamer pool in the next round of SELEX.

To evaluate the changing affinity of the aptamer pool with each round of SELEX, fluorescence-linked or enzyme-linked methods are employed. MSCs are cultured to confluence in a 96-well imaging plate. Biotinylated and FITC-tagged aptamers from each round are denatured and renatured as described above and incubated in appropriate wells for 30 mins at 37 C and 5% CO2. In fluorescence-linked assays, wells are aspirated and washed three times with excesses of phosphate buffered saline (PBS) to remove non-binding sequences. Fluorescent signal per well from the remaining binding sequences is then measured via fluorescence scanner, it being understood that a greater level of signal corresponds to a greater number of binding sequences. In enzyme-linked assays, wells are aspirated (post aptamer incubation) and a streptavidin-horseradish-peroxidase (HRP) conjugate is added to the wells for 30 mins. This is then aspirated and the wells are washed three times with excesses of phosphate buffered saline (PBS) to remove non-binding sequences and unbound streptavidin-HRP. An excess of colorimetric substrate of the HRP enzyme is then added to each well, and the plate is covered from light for 20-30 mins to allow the enzyme to react. Color intensity per well is then measured on a spectrophotometer, it being understood that a greater level of signal corresponds to a greater number of binding sequences.

Example 2

Fluorescently Tagged Aptamers were Immobilized in an Amphiphilic Film of on a Tantalum Metal Medical Implant Avidin, an amphiphilic molecule, was dissolved in phosphate buffered saline (PBS) at a concentration of 200 ug/mL. This solution was then added to a liquid olefin (specifically, oleic acid) at a ratio of 1:1 by volume, and an emulsion was created via vigorous shaking. The surface of a tantalum medical implant was then exposed to the emulsion such that a thin film olefin layer formed on the surfaces of the implant and an avidin nanofilm at the interface between the olefin layer and the surrounding saline solution. The resulting nanofilm had the active binding sites of the avidin presented on the PBS side in a dense configuration. Additional PBS was used to irrigate the matrix and remove excess avidin bearing solution.

Aptamers of interest were conjugated with biotin at their 5' end and a fluorescent molecule at their 3' end. The tantalum metal with the amphiphilic film was then exposed to a solution of biotinylated/fluorescent tagged aptamers in PBS such that the biotin conjugated with the immobilized avidin and presented a dense surface of fluorescent aptamers at the PBS interface. The matrix was washed again with PBS to remove unbound sequences and fluorescent scanning was used to detect the presence of the remaining fluorescently tagged surface immobilized aptamers on the medical implant (FIG. 1B). The experiment was repeated without the presence of the oleic acid film to demonstrate that the results were the result of an amphiphilic film forming on the non-polar liquid. No significant fluorescence was detected in the control (FIG. 1A)

indicating that aptamer immobilization was due to the mechanisms described in the present invention.

Example 3

MSC Capture and Immobilization on a Tantalum Metal Medical Implant Utilizing Aptamers Amphiphilic molecules are produced with a hydrophilic head of human MSC specific aptamers and a hydrophobic hydrocarbon tail of the form (CH2)n, with n in the range of 8 to 24. The molecules are suspended in a sterile normal saline solution at a density of 240 ug/ml and packaged in a 10 ml sealed glass vial for delivery to surgery, along with a 10 ml sealed glass vial of sterile oleic acid. In surgery, a sterilized Trabecular Metal™ bone implant is place in a dish and the oleic acid is poured onto the implant in a manner which allows the material to flow by gravity through the pores of the device; the implant is further rotated in contact with the oleic acid to provide good distribution and then removed from the dish to allow excess material to drain. The implant is then placed in a close-fitting plastic sleeve and the aptamer solution is injected into the sleeve. The sleeve is then sealed and agitated for two minutes. A sterile saline solution purge is used to remove unbound aptamer in solution. Excess saline solution is drained and immediately replaced by a stem cell rich portion of bone marrow aspirate from the patient. The implant is then placed into the intended point of repair in the patient.

Example 4

Figure 2A:
FIGS. 2a, b and c are 4× microscopic images of human mesenchymal stem cells (MSC) on glass slides. All three slides were exposed to solutions with the same concentration of stem cells.
Figure 2B:
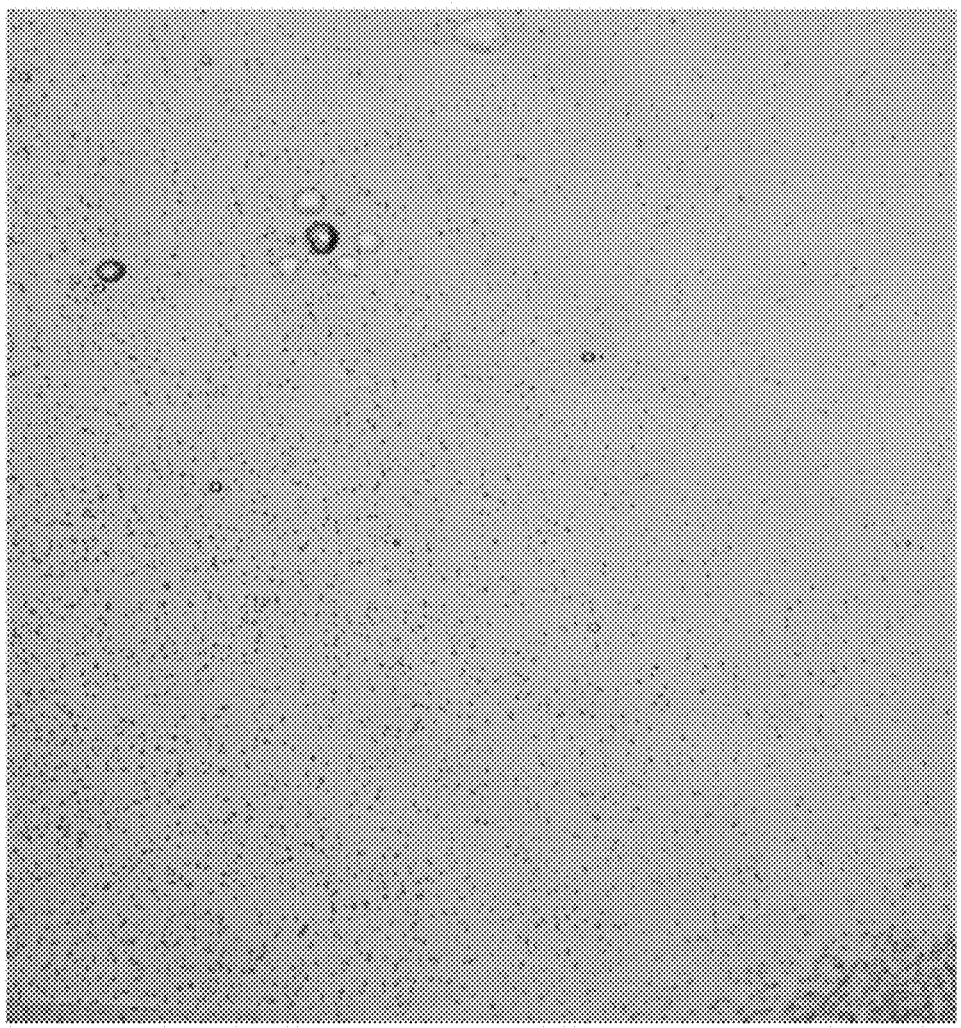
In FIG. 2b, antibodies with an affinity for MSC has been introduced into solution.
Figure 2C:
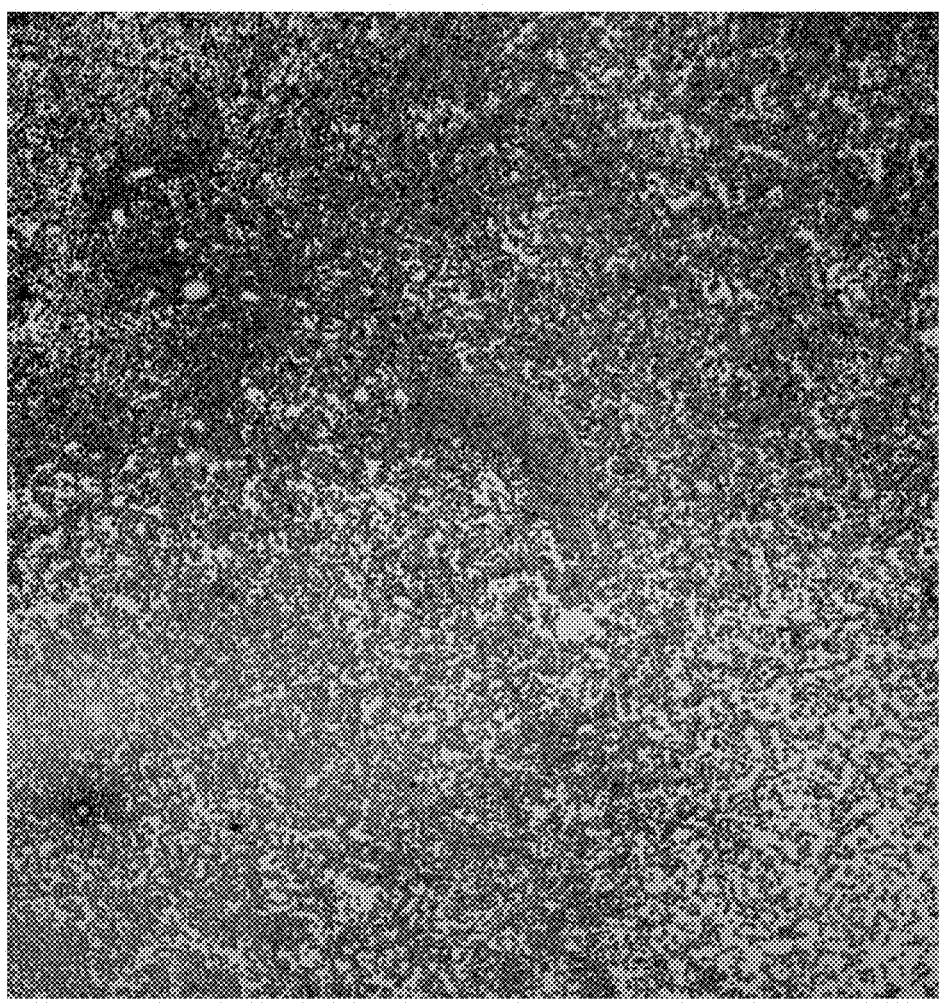
In FIG. 2c, the slide has been first treated in accordance with the present invention with a non-polar liquid film and an amphiphilic surface film incorporating antibodies with an affinity for MSC. A four-fold increase in stem cell immobilization was realized when the slide was treated in accordance with the present invention.
Figure 3:
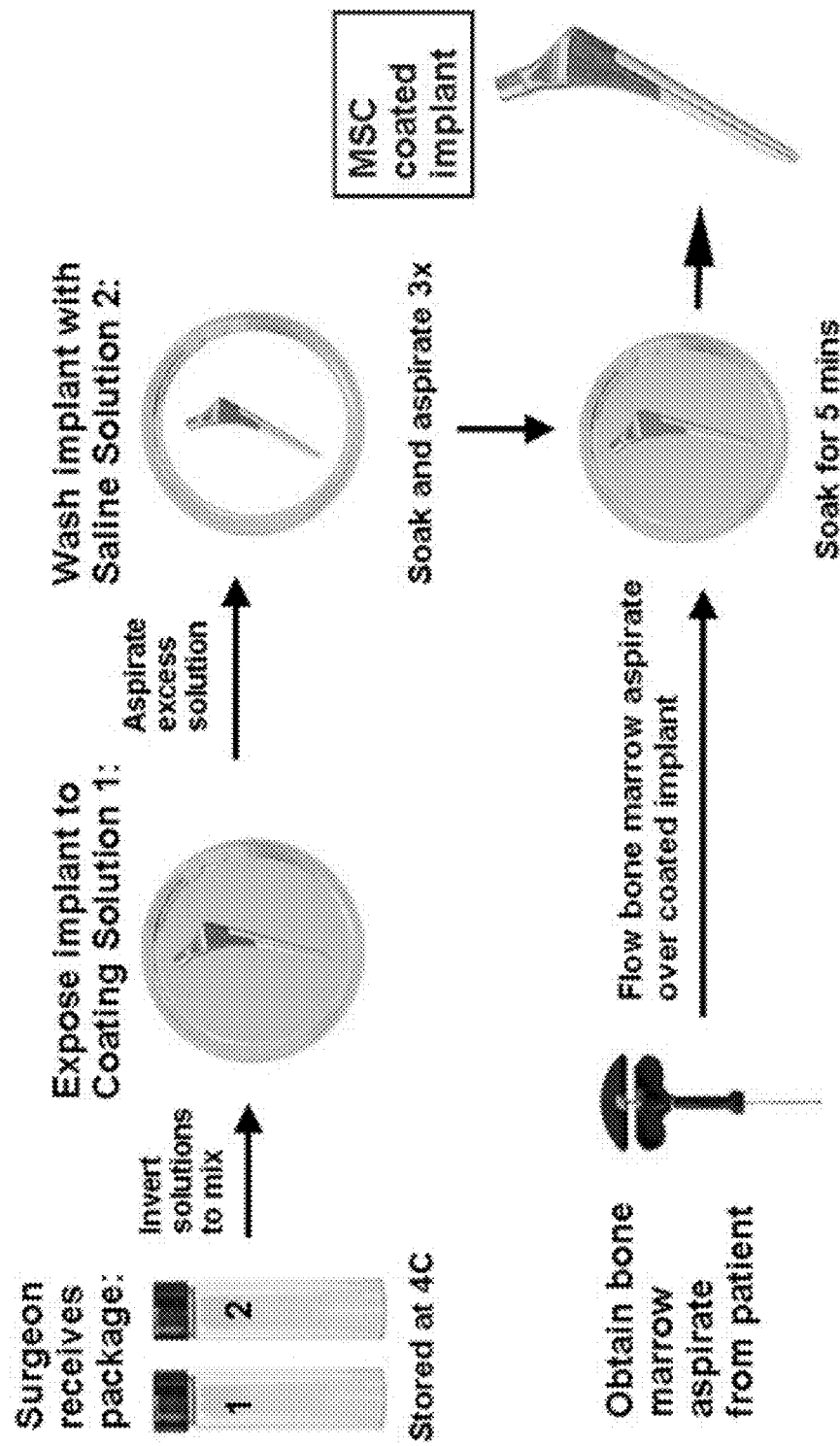
FIG. 3 depicts a suitable sequence for use of solutions of the present invention by a surgical team in an operating room environment to coat a surgical implant with a patients own stem cells, extracted at the time of surgery.
Figure 4:
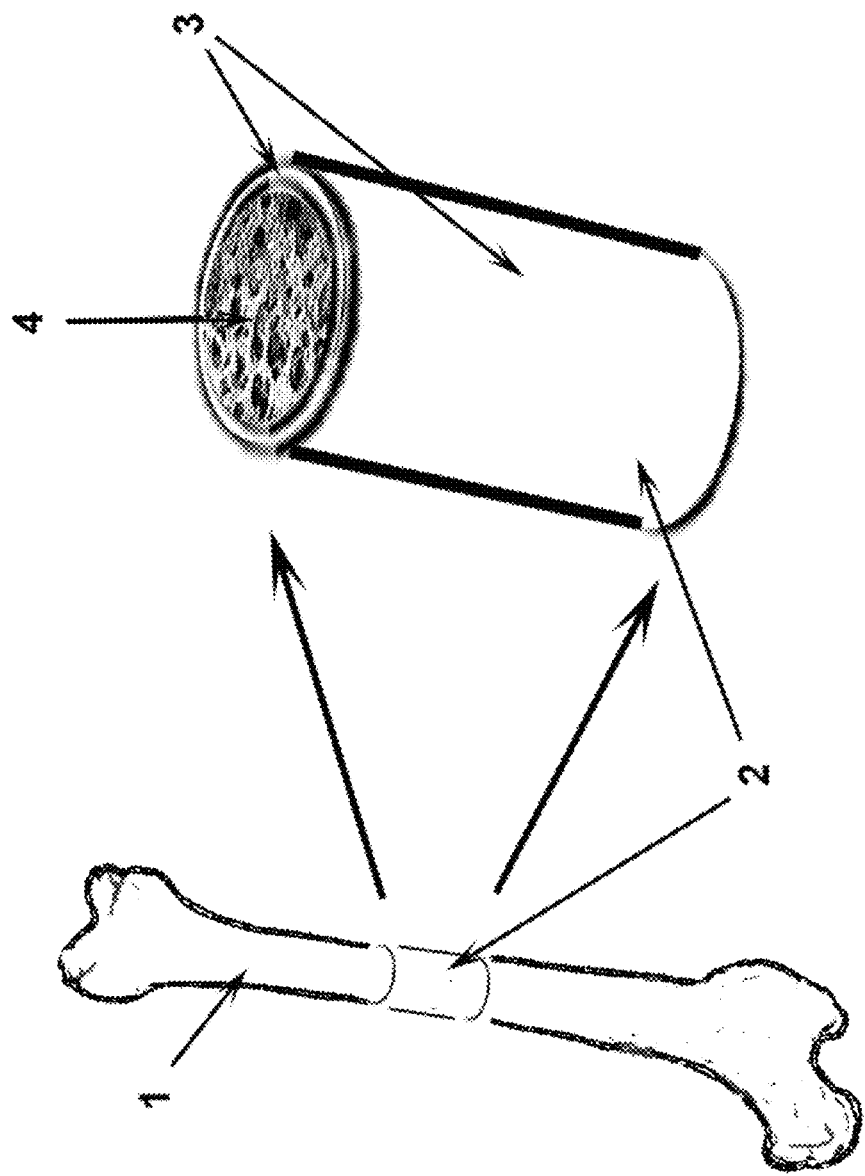
FIG. 4 depicts a bone (1) with a Trabecular Metal™ prosthetic implant (2) inserted in a non-union. The circumferential band (3) of the implant has been impregnated with a biodegradable wax that constrains liquid transport to and from the interior through the ends of the implant (4), which abut the bone. The porous metal on the interior of the implant is saturated with bone marrow aspirate prior to the implant being inserted into the point of non-union. The net result is that the bioactive materials in the implant are constrained to interact with the adjacent bone at the points where ingrowth is being promoted.

MSC Capture and Immobilization on a Tantalum Metal Medical Implant Utilizing Antibodies Avidin was dissolved in phosphate buffered saline (PBS) at a concentration of 200 ug/mL and mixed with an equivalent volume of liquid olefin. The mixture was vigorously shaken to create an emulsion, and this was introduced to the matrices, an 8 $mm^3$ cube of Trabecular Metal™ (tantalum) and a glass cover slip. Excess liquid was aspirated and a biotinylated antibody dissolved in PBS was introduced to the matrices at a molar equivalent to the avidin in the film. This antibody was specific to the antigen CD271, or low-affinity nerve growth factor receptor (LNGFR), which is a marker used to characterize human mesenchymal stem cells (hMSCs). Excess liquid was again aspirated, and a suspension of ~2×105 hMSCs (Passage 2) was added to the matrices and incubated with it for 2 hours. To evaluate the effectiveness of the film, the matrices were washed four times with an excess of PBS to remove unbound cells. For the glass matrix, remaining cells were then counted via light microscopy. For the tantalum matrix, a luminescence-based assay was used to calorimetrically quantify remaining cells (CellTiter-Glo® Luminescent Cell Viability Assay by Promega). The matrix was incubated with enzyme and colorimetric substrate for 10 mins, before being scanned on a luminometer. The construct of the present invention exhibited a 400% increase in stem cell binding to the substrate over the untreated tantalum. FIGS. 2a, b and c are photographic images from this work.

Example 5

Bone Trabecular Metal™ Prosthetic Implant with P-selectin Surface Immobilized in Wax A bioabsorbable polymeric wax in melted form is passed through a tantalum metal prosthetic bone implant which has 80% open area, such that the internal surfaces of the implant become coated with melted wax. A solution of P-selectin is then passed through the implant, such that the amphiphilic molecules of P-selectin become immobilized in the surface of the wax. The non-bone mating surfaces of the implant are then to a depth of 4 cm with a highly viscous hydrogenated oleic acid with embedded BMP-2 and FGF. Bone marrow which has been extracted from the prospective patient is then diluted and placed in a device comprising hydraulic seals to two uncoated faces of the implant and a pump device. The bone marrow is then pumped through the implant such that stem cells in the marrow are affixed to the P-selectin treated surfaces. The implant is then placed in the patient.

Example 6

Bone Prosthetic Implant with Non-bone Mating Surfaces Sealed

The pore surfaces in a tantalum metal prosthetic bone implant which has 80% open area, are coated with polyethylene glycol (PEG). The PEG surfaces are then biotinylated and P-selectin is immobilized on the biotinylated PEG coated surfaces of the pores of the implant. The non-bone mating surfaces of the implant are then sealed to a depth of 4 cm with a highly viscous hydrogenated oleic acid with embedded BMP-2 and FGF. Bone marrow which has been extracted from the prospective patient is then diluted and placed in a device comprising hydraulic seals to two uncoated faces of the implant and a pump device. The bone marrow is then pumped through the implant such that stem cells in the marrow are affixed to the P-selectin treated surfaces. The implant is then placed in the patient.

Example 7

Micelles in Titanium Dental Implant

Herein, a dental implant composed of an enamel cap over a sintered titanium core and root is utilized. BMP-2, FGF and serum albumin are placed in a sterile saline solution, oleic acid is added to the solution at a one to three ratio. The resulting mixture is then agitated and solicited to form micelle structures in the 100 nm to 100 um range. The dental implant is placed in a device which hydraulically seals the perimeter and provides a liquid entry port on one side of the implant and a liquid discharge port on the other side. The solution is circulated by pump through the implant for 30 minutes and the implanted in the patient.

Industrial Applicability

Procedures that can be shown to speed recovery and/or increase the success rate of surgical intervention are of high value. Medical device coatings that incorporate growth factors and anti-inflammatory molecules into surface films to trigger or impair biological responses have been proposed; however, the effects of such films are limited by the diffusion and subsequent dilution of these molecules over time. Furthermore, while stem cells, growth factors and other bioactive materials have been shown to provide therapeutic benefits in the treatment of musculoskeletal conditions, available techniques for retaining and immobilizing such materials in a scaffold of interest are significantly limited.

Most useful biological signaling molecules are produced by various biological cells; consequently, a far more powerful technology, enabling a more sustained level of signaling molecules in an area beyond that which is achievable by introduction of a set number of molecules during surgery, would be to actually immobilize the signaling molecule producing biological cells in the target area of interest. Immobilization of stem cells in an area is of particular value since they are known to produce both signaling chemicals, which attract other stem cells to a region, as well as immunomodulatory chemicals, which reduce swelling and scar tissue formation.

The benefit of a cell-selective, nanofilm-coated implant of the present invention is three-fold. First, a cell-selective surface can serve to concentrate stem (or other targeted) cells from a solution, particularly a solution containing the patient's own cells, eliminating concerns about incompatibility or infection from allograft tissue. Second, the immobilization of stem cells will locally enhance the known effects of these cells in secreting growth factors to regenerate tissue and reduce healing time. Third, the autologous stem cell-coated nanofilm will serve as a biomimetic scaffold that not only stimulates osteogenesis but also reduces immune response to the foreign implant.

Accordingly, the ability to selectively concentrate and immobilize biological cells on any surface is of great value in evolving fields of medicine. The technology of the present invention not only achieves this end but does so in a manner which is compatible with existing surgical devices and techniques and which can be performed by the surgical team using autograft stem cells, such as those contained in bone marrow. Additionally, because the present invention is based on the science of amphiphilic films, the cell binding moieties can be presented at a theoretical maximum density on the surface.

The benefit of a cell-selective, nanofilm-coated implant is three-fold. First, a cell-selective surface can serve to concentrate stem (or other targeted) cells from a solution, particularly a solution containing the patient's own cells, eliminating concerns about incompatibility or infection from allograft tissue. Second, the immobilization of stem cells will locally enhance the known effects of these cells in secreting growth factors to regenerate tissue and reduce healing time. Third, the autologous stem cell-coated nanofilm will serve as a biomimetic scaffold that not only stimulates tissue growth but also reduces immune response to the foreign implant.

All patents and publications mentioned herein are incorporated by reference in their entirety. Nothing herein is to be construed as an admission that the invention is not entitled to antedate such disclosure by virtue of prior invention.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Other advantages and features will become apparent from the claims filed hereafter, with the scope of such claims to be determined by their reasonable equivalents, as would be understood by those skilled in the art. Thus, the invention shall be defined not by the above description, but by the following claims and their equivalents.

What is claimed:

1. A method of constructing a target cell-carrying medical implant device, said method comprising the steps of:
    a. providing a porous biocompatible medical implant comprising a solid exterior surface having a plurality of pores;
    b. providing a solution comprised of the following components: (i) a non-polar liquid, (ii) a polar liquid and (ii) a plurality of amphiphilic molecules composed of hydrophobic tail ends and hydrophilic head ends, wherein said head ends have a binding affinity for one or more target cells, further wherein said solution components assemble into non-polar-liquid-filled micelles or micelle-like constructs;
    c. contacting said micelles or micelle-like constructs with a solution containing target cells to which the hydrophilic head ends of said amphiphilic molecules have a binding affinity and inducing said micelles or micelle-like constructs to bind said target cells and form micelle-target cell units; and
    d. introducing said micelle-target cell units into the pores of said implant exterior surface so as to yield a medical implant device having target cells immobilized within said exterior surface pores.

2. The method of claim 1, wherein at least one of said hydrophilic head ends comprises a nucleic acid aptamer.

3. The method of claim 1, wherein said hydrophilic head ends comprise two or more nucleic acid aptamers having different structures and different binding affinities.

4. The method of claim 1, where said target cell is a stem cell.

5. The method of claim 1, wherein said solution of step (b) further comprises said target cells.

6. The method of claim 1, wherein step (c) is performed in an operating room environment.

7. The method of claim 1, wherein said target cells are autologous tissue of the patient.

8. The method of claim 1, further comprising the step of inducing a fraction of said micelle-target cell units to coalesce once introduced in the pores of said medical device through one or more factors selected from the group consisting of mechanical action, increased temperature, and changes in pH.

9. The method of claim 1, wherein said non-polar-liquid-filled micelles or micelle-like constructs comprise oil-in-water emulsions or water-in-oil emulsions.

10. The method of claim 9, wherein said medical device is selected from the list including a wound dressing, a tissue scaffold, a vertebral implant, a vascular implant, an intraluminal device, an anastomosis structure, a haemostatic barrier, a surgical suture and bone, cartilage and tooth implants.

* * * * *